United States Patent
Brown et al.

(10) Patent No.: US 9,387,018 B2
(45) Date of Patent: Jul. 12, 2016

(54) SURGICAL IMPLANT SYSTEM AND METHOD

(71) Applicant: Warsaw Orthopedic, Inc., Warsaw, IN (US)

(72) Inventors: Richard Quinn Brown, Collierville, TN (US); Daniel Paxton Wall, Cordova, TN (US); Jeff R. Justis, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 142 days.

(21) Appl. No.: 13/827,287

(22) Filed: Mar. 14, 2013

(65) Prior Publication Data

US 2014/0277197 A1  Sep. 18, 2014

(51) Int. Cl.
*A61B 17/70* (2006.01)

(52) U.S. Cl.
CPC .................................. *A61B 17/7086* (2013.01)

(58) Field of Classification Search
CPC ........... A61B 17/7083; A61B 17/7085; A61B 17/7086; A61B 17/7088; A61B 17/7089
See application file for complete search history.

(56) References Cited

U.S. PATENT DOCUMENTS

| | | | |
|---|---|---|---|
| 6,755,338 B2 | 6/2004 | Hahnen et al. | |
| 7,186,030 B2 | 3/2007 | Schlanger | |
| 7,371,239 B2 | 5/2008 | Dec et al. | |
| 7,462,182 B2 | 12/2008 | Lim | |
| 7,476,240 B2 | 1/2009 | Raymond et al. | |
| 7,481,813 B1 | 1/2009 | Purcell | |
| 7,497,869 B2 | 3/2009 | Justis | |
| 7,520,879 B2 | 4/2009 | Justis et al. | |
| 7,563,274 B2 | 7/2009 | Justis et al. | |
| 7,572,276 B2 | 8/2009 | Lim et al. | |
| 7,597,694 B2 | 10/2009 | Lim et al. | |
| 7,648,507 B2 | 1/2010 | Techiera et al. | |
| 7,686,809 B2 | 3/2010 | Triplett et al. | |
| 7,695,475 B2 | 4/2010 | Justis et al. | |
| 7,758,584 B2 | 7/2010 | Bankoski et al. | |
| 7,914,558 B2 | 3/2011 | Landry et al. | |
| 7,998,144 B2 | 8/2011 | Schumacher et al. | |
| 8,025,682 B2 | 9/2011 | Mahoney et al. | |
| 8,043,343 B2 | 10/2011 | Miller et al. | |
| 8,075,592 B2 | 12/2011 | Landry et al. | |
| 8,100,951 B2 | 1/2012 | Justis et al. | |
| 8,142,437 B2 | 3/2012 | McLean et al. | |
| 8,167,887 B2 | 5/2012 | McLean | |
| 8,192,439 B2 | 6/2012 | Songer et al. | |
| 8,206,394 B2 | 6/2012 | Stad et al. | |
| 8,246,624 B2 | 8/2012 | Forton et al. | |

(Continued)

FOREIGN PATENT DOCUMENTS

| | | |
|---|---|---|
| DE | 10032126 | 1/2002 |
| EP | 1916954 | 5/2008 |

(Continued)

*Primary Examiner* — Eduardo C Robert
*Assistant Examiner* — Julianna N Harvey

(57) ABSTRACT

A surgical instrument includes a first member extending between a first end and a second end. A second member extends between a first end and a second end. A third member is connected to the first end of the first member to relatively translate the second ends. The third member includes a part and a locking element engageable with the part. The part is disposable in a first locking orientation, a second locking orientation and a non-locking orientation. Systems and methods of use are disclosed.

20 Claims, 19 Drawing Sheets

(56) References Cited

U.S. PATENT DOCUMENTS

| | | | |
|---|---|---|---|
| 8,308,728 B2 | 11/2012 | Iott et al. | |
| 8,348,954 B2 | 1/2013 | Carls et al. | |
| 8,366,714 B2 | 2/2013 | Jones et al. | |
| 8,460,301 B2 | 6/2013 | Fiorella | |
| 2003/0225408 A1* | 12/2003 | Nichols | A61B 17/7032 606/86 A |
| 2005/0090824 A1* | 4/2005 | Shluzas et al. | 606/61 |
| 2005/0192587 A1* | 9/2005 | Lim | 606/86 |
| 2005/0192589 A1 | 9/2005 | Raymond et al. | |
| 2007/0078460 A1 | 4/2007 | Frigg et al. | |
| 2007/0123904 A1 | 5/2007 | Stad et al. | |
| 2007/0213714 A1* | 9/2007 | Justis | 606/61 |
| 2007/0233184 A1* | 10/2007 | Wong | A61B 17/7083 606/205 |
| 2008/0077138 A1* | 3/2008 | Cohen | A61B 17/7083 606/86 A |
| 2008/0121234 A1 | 5/2008 | Ho et al. | |
| 2008/0269764 A1 | 10/2008 | Blain et al. | |
| 2008/0269805 A1 | 10/2008 | Dekutoski et al. | |
| 2008/0312703 A1* | 12/2008 | Hestad | A61B 17/7085 606/86 A |
| 2009/0198281 A1 | 8/2009 | Rice et al. | |
| 2010/0036443 A1 | 2/2010 | Hutton et al. | |
| 2010/0249856 A1 | 9/2010 | Iott et al. | |
| 2011/0022088 A1* | 1/2011 | Forton et al. | 606/246 |
| 2011/0077690 A1 | 3/2011 | Shin et al. | |
| 2011/0093014 A1 | 4/2011 | Davis et al. | |
| 2011/0166610 A1 | 7/2011 | Altarac et al. | |
| 2011/0184464 A1 | 7/2011 | Fiorella | |
| 2011/0196426 A1 | 8/2011 | Peukert et al. | |
| 2011/0202096 A1 | 8/2011 | White et al. | |
| 2011/0218581 A1* | 9/2011 | Justis | 606/86 A |
| 2011/0313470 A1* | 12/2011 | McLean | A61B 17/7011 606/305 |
| 2012/0022597 A1 | 1/2012 | Gephart et al. | |
| 2012/0029580 A1* | 2/2012 | Solitario, Jr. | 606/86 A |
| 2012/0271355 A1 | 10/2012 | Steele et al. | |
| 2013/0012984 A1* | 1/2013 | Wall | 606/206 |
| 2013/0018423 A1 | 1/2013 | Stad et al. | |

FOREIGN PATENT DOCUMENTS

| | | |
|---|---|---|
| EP | 2111809 | 10/2009 |
| KR | 10-2008-0059920 | 8/2008 |
| KR | 10-2009-0072327 | 1/2010 |
| KR | 10-1001539 | 12/2010 |
| KR | 10-2011-0029988 | 9/2011 |

* cited by examiner

SURGICAL IMPLANT SYSTEM AND METHOD

TECHNICAL FIELD

The present disclosure generally relates to medical devices for the treatment of musculoskeletal disorders, and more particularly to a surgical implant system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. This disclosure describes an improvement over these prior art technologies.

SUMMARY

In one embodiment, a surgical instrument is provided. The surgical instrument includes a first member extending between a first end and a second end. A second member extends between a first end and a second end. A third member is connected to the first end of the first member to relatively translate the second ends. The third member includes a part and a locking element engageable with the part. The part is disposable in a first locking orientation such that the second ends engage a spinal construct, a second locking orientation such that the part disengages the locking element and is biased relative to the third member and a non-locking orientation such that the part is moved relative to the third member and the second locking orientation such that the second ends are disposed to disengage the spinal construct.

BRIEF DESCRIPTION OF THE DRAWINGS

The present disclosure will become more readily apparent from the specific description accompanied by the following drawings, in which.

DETAILED DESCRIPTION

Figure 1:
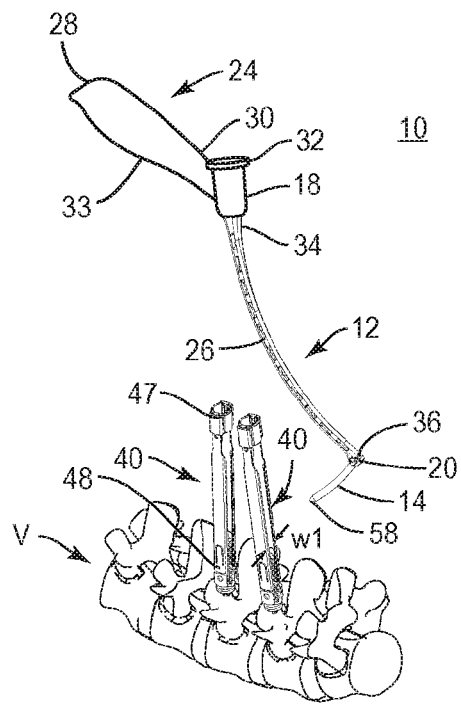
FIG. 1 is a perspective view of components of one embodiment of a surgical implant system in accordance with the principles of the present disclosure disposed with vertebrae.

The exemplary embodiments of the surgical implant system and related methods of use disclosed are discussed in terms of medical devices for the treatment of musculoskeletal disorders and more particularly, in terms of a surgical implant system for implant delivery to a surgical site and a method for treating a spine.

In one embodiment, the surgical implant system is employed with a method that includes inserting a rod through the same stab incision in which a pedicle screw was placed percutaneously. In one embodiment, the system includes a surgical instrument, such as, for example, a rod inserter. In one embodiment, the surgical instrument clamps an implant, such as, for example, a longitudinal rod, by pulling a flexible shaft through a cannulated main body of the rod inserter. In one embodiment, the proximal end of the flexible shaft is threaded and mates with an internally threaded knob that is captured in the handle by a pin/slot feature. In one embodiment, the knob provides adjustability of a clamping force on the rod. In one embodiment, the knob is retained in an upper handle by a pin and is freely rotatable. In one embodiment, the knob is rotatable to feed the thread of a clamp shaft and moves the shaft up and down. In one embodiment, the shaft is keyed by a pin to prevent rotation and/or provide a stop axially in both directions. In one embodiment, as the captured knob is turned, the rod is either secured to or released from the inserter depending on the direction of rotation of the knob. In one embodiment, the threaded clamping mechanism is replaced with a linkage mechanism that moves the flexible shaft for clamping and releasing the rod. In one embodiment, the rod is clamped relatively perpendicular to the main shaft.

In one embodiment, the system includes a surgical instrument, such as, for example, a rod inserter that can be used with extended tab screws or other extenders with an extended rod guide. In one embodiment, the rod is initially placed, inclined relative to the extenders, in a stab incision in which a pedicle screw has been placed percutaneously. The rod is moved to the surgical site such that the rod is inclined relative to the extenders. As the rod is moved closer to a saddle of a pedicle screw, the rod is rotated to a position within a first and at least a second pedicle screw. Once in place, the rod is released. In one embodiment, the inserter shaft remains outside the screw extenders. In one embodiment, the shaft resides between two extensions attached to a pedicle screw or within a feature of an extender. In one embodiment, the geometry of the shaft allows the mechanism to have three functional components and a handle. In one embodiment, the angle of the handle and geometry of the main shaft facilitates the rod being inserted starting relatively parallel to an extender and ending relatively perpendicular to the extender. In some embodiments, the method includes inserting a rod percutaneously without the need to make a third incision.

In one embodiment, the system includes a surgical instrument, such as, for example, a rod inserter having a two-clamp lever that overcomes, for example, over-tightening of a tension adjustment mechanism. In one embodiment, the rod inserter includes a latch lock release button. In one embodiment, the lock release button is pushed to release a spring loaded clamp lever causing the clamp lever to rotate a distance away from the rod inserter body, prior to an over center cam being disengaged. This configuration provides a user with an improved grip on the lever to overcome over tightening of the adjustment mechanism. In one embodiment, driving the lever in a downward motion causes a feature on an end of the clamp lever to engage a main clamp lever. In one embodiment, continued driving of the lever causes the main clamp lever to push a translation sleeve down, opening clamps at a distal end of the rod inserter, and disengaging an implant, such as, for example, a longitudinal rod. In one embodiment, driving the lever until it snaps into the latch lock release button causes the clamps to close to engage the longitudinal rod. In one embodiment, the lever is spaced apart from the surface of the rod inserter body to provide additional leverage to overcome the over center cam.

In one embodiment, the surgical instrument, such as, for example, a rod inserter includes a tension adjustment mechanism using a hex socket style adjustment. In one embodiment, inserting a hex key into the socket turns a latch pull shaft threaded with a rod inserter clamp shaft to increase or decrease tension of the clamp. In one embodiment, the latch pull shaft is attached to a translation sleeve and is allowed to rotate in relation to the translation sleeve, which translates axially. In one embodiment, the rod inserter includes a leaf spring detent system so that a user turns the adjustment shaft to set clamp force without any additional step being required. In one embodiment, the detent system holds the shaft in place reducing the steps required to adjust the tension.

In one embodiment, the surgical instrument includes a rod inserter having an outer sleeve configured to fit between tab extenders and a clamp at its distal end configured not to fit between tab extenders. This configuration resists and/or prevents having a cone end of a spinal rod inside the tulip head of a bone screw. In one embodiment, the cone of the spinal rod is maintained outside of the tulip head so that the set screw clamps on the outer diameter of the rod to provide maximum grip strength. In one embodiment, the sides of the rod inserter clamps include bosses that resist and/or prevent the clamp from entering too far into the extender or screw tulip. In one embodiment, the bosses of the clamp can slide along the rails of the extenders during rod insertion preventing the cone of the rod from entering too deep into the tulip head.

In one embodiment, the surgical instrument includes a percutaneous rod inserter having a silicone handle, a clamp mechanism and clamps. In one embodiment, the surgical instrument includes a two stage clamp mechanism having a latch lock release button, a main clamp lever, a clamp lever and a torsion spring. In one embodiment, pressing the latch lock release button releases the clamp lever from a first locking orientation and the torsion spring causes the clamp lever to pop up about 30 degrees to a second locking orientation. In the second locking orientation, the clamp lever is open to provide a practitioner more purchase on the lever to overcome an over center cam and the main clamp lever does not move and the cam is still over center. A feature on the clamp lever engages a slot on the main clamp lever and applying force to the clamp lever engages the main clamp lever and releases the over center cam to a non-locking orientation, which opens the jaws. In one embodiment, the translation sleeve is pushed down. To close the jaws, the clamp lever is pushed to re-engage the main clamp lever and force is applied until the clamp lever snaps into the latch lock release lever and the over center cam is engaged in a locking orientation, clamping the rod.

In one embodiment, the inserter body includes a cam surface engageable with a cam surface of the clamp lever. The cam surface of the clamp lever cams off the cam surface of the inserter body to aid in overcoming the over center cam. In one embodiment, the system includes a hex key that is inserted into a socket to turn a latch pull shaft rod connected to an inserter clamp shaft connected to the clamps. The latch pull shaft threads with the rod inserter clamp shaft axially to increase or decrease tension of the clamps. A translation sleeve moves axially as the clamp system is actuated. The latch pull shaft is attached to the translation sleeve via a C-clip and is allowed to rotate in relation to the translation sleeve. A detent spring prevents inadvertent rotation of the latch pull shaft and serves as a lock.

In one embodiment, one or all of the components of the system are disposable, peel-pack, pre-packed sterile devices used with an implant. One or all of the components of the system may be reusable. The system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical implant system and related methods of employing the surgical implant system in accordance with the principles of the present disclosure. Alternate embodiments are also disclosed. Reference will now be made in detail to the exemplary embodiments of the present disclosure, which are illustrated in the accompanying figures. Turning to FIGS. 1-5, there are illustrated components of a surgical system, such as, for example, a surgical implant system 10 in accordance with the principles of the present disclosure.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 is employed, for example, with a minimally invasive procedure, including percutaneous techniques, mini-open and open surgical techniques to deliver and introduce an implant, such as, for example, a spinal construct, at a surgical site within a body of a patient, for example, a section of a spine. In some embodiments, system 10 may include and/or deliver and introduce implants such as spinal rods, bone fasteners, connectors, plates and interbody devices.

System 10 includes a surgical instrument 12 that is configured for engagement with a spinal construct, such as, for example, a spinal rod 14. Instrument 12 includes a first member, such as, for example, a flexible inner shaft (not shown), which has a cylindrical cross-section configuration. In some embodiments, the inner shaft may have variously configured cross-sections, such as, for example, round, oval, rectangular, polygonal, irregular and/or tapered.

The inner shaft extends between a first end 18 and a second end 20 of instrument 12. The inner shaft includes a clamp, such as, for example, a jaw 22 that is configured for engagement with spinal rod 14. End 18 is configured for engagement with a part, such as, for example, a knob portion 32. The inner shaft is configured for engagement with knob portion 32 to cause the translation of the inner shaft along a radius of curvature. End 18 is threadedly engaged to knob portion 32. Knob portion 32 is rotatable such that the inner shaft translates along the radius of curvature. The inner shaft includes a range of translation between a proximal most position and a distal most position. In some embodiments, the inner shaft may axially translate.

Instrument 12 includes a second member, such as, for example, a sleeve 26. Sleeve 26 defines an inner cavity configured for disposal of the inner shaft. The inner shaft is translatable within and relative to sleeve 26. Sleeve 26 extends between a proximal end 34 and distal end 36. Distal end 36 of sleeve 26 includes a clamp, such as, for example, a jaw 38. Jaw 38 is configured for engagement with spinal rod 14. Proximal end 34 of sleeve 26 is attached to knob portion 32. As knob portion 32 is actuated, the inner shaft translates within and relative to sleeve 26 causing jaw 22 of the inner shaft to move adjacent and/or engage jaw 38 to capture spinal rod 14 and/or space from jaw 38 to release spinal rod 14. Actuation of knob portion 32 includes, such as, for example, rotation in a clockwise or counter-clockwise direction. In some embodiments, relative movement of jaws 22, 38 may be facilitated with relative axial translation of the inner shaft and sleeve 26.

Instrument 12 includes a third member, such as, for example, a handle 24 and knob portion 32. Handle 24 extends between a first end 28 and a second end 30. First end 28 of handle 24 includes an ergonomic hand portion 33 for manipulation thereof. Second end 30 of handle 24 is connected to and includes knob portion 32.

System 10 includes a plurality of extenders 40 extending perpendicularly from vertebrae V. Each extender 40 extends between a proximal end 47 and a distal end 48. Each extender 40 includes a first wall, such as, for example, a rail 42 and a second wall, such as, for example, a rail 44. Rails 42, 44 define a passageway 52 therebetween. Passageway 52 extends between proximal ends 47 and distal ends 48 of each extender 40. Distal end 48 of passageway 52 includes an implant cavity 46. Implant cavity 46 defines a width dimension w1 between rails 42, 44 configured for the passage of spinal rod 14. Passageway 52 has a uniform thickness dimensioned such that sleeve 26 can pass therethrough. In some embodiments, all or only a portion of passageway 52 may have alternate cross section configurations, such as, for example, oval, oblong, triangular, square, polygonal, irregular, uniform, non-uniform, offset, staggered, and/or tapered. Extenders 40 include caps 50 disposed at proximal ends 47 of extenders 40.

In assembly, operation and use, system 10, similar to that described above, is employed with a surgical procedure for treatment of a spinal disorder affecting a section of a spine of a patient, as discussed herein. System 10 may also be employed with other surgical procedures. For example, system 10 can be used with a surgical procedure for treatment of a condition or injury of an affected section of the spine including vertebrae V.

In use, to treat the affected section of vertebrae V, a medical practitioner obtains access to a surgical site including vertebrae V in any appropriate manner, such as through incision and retraction of tissues. In some embodiments, system 10 may be used in any existing surgical method or technique including open surgery, mini-open surgery, minimally invasive surgery, and percutaneous surgical implantation, whereby vertebrae are accessed through a micro-incision, or sleeve that provides a protected passageway to the area. Once access to the surgical site is obtained, the particular surgical procedure is performed for treating the spinal disorder. The components of system 10 are then employed to augment the surgical treatment. System 10 can be delivered or implanted as a pre-assembled device or can be assembled in situ. One or all of the components of system 10 may be completely or partially revised, removed or replaced during or after the surgical procedure.

One or a plurality of incisions are made in the body of a patient and a cutting instrument (not shown) creates one or a plurality of surgical pathways and/or openings for implantation of components of system 10. For example, system 10 is employed with a percutaneous surgical implantation such that a stab incision creates a surgical pathway for delivering a bone fastener, such as, for example, a pedicle screw 54 to the surgical site. A preparation instrument (not shown) can be employed to prepare tissue surfaces of vertebrae V, as well as for aspiration and irrigation of a surgical region according to the requirements of a particular surgical application.

Jaws 22, 38 are disposed adjacent spinal rod 14 and in a non-locking and open orientation. Knob portion 32 of instrument 12 is rotated in a counter-clockwise direction causing the inner shaft to translate in a proximal direction relative to sleeve 26 causing jaws 22, 38 to move to a locking and closed orientation to capture spinal rod 14.

Pilot holes or the like are made in vertebrae V for receiving the shaft of pedicle screws 54. Components of system 10 including extenders 40 are disposed adjacent vertebrae V at the surgical site and the components of system 10 are manipulable to fix or otherwise connect pedicle screws 54 with vertebrae V, according to the particular requirements of the surgical treatment. Pedicle screws 54 are fastened with vertebrae V. A driver (not shown) may be employed with extenders 40 to fix pedicle screws 54 with vertebrae V.

Spinal rod 14 is delivered through the stab incision inclined relative to the extenders 40 along the pathway, which pedicle screw 54 has been placed percutaneously, to the surgical site, as shown in FIG. 1. Handle 24 is manipulated such that sleeve 26 is disposed transverse to extenders 40 and spaced above extenders 40. Spinal rod 14 is inclined relative to the extenders 40 and a distal end 58 of spinal rod 14 is oriented in a direction towards vertebrae V.

Figure 2:
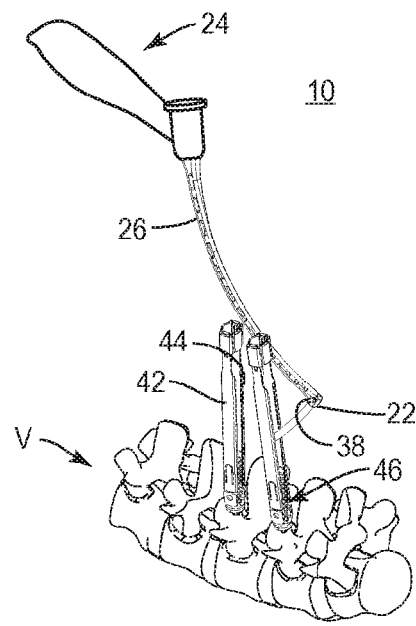
FIG. 2 is a perspective view of the components and vertebrae shown in FIG. 1.
Figure 3:
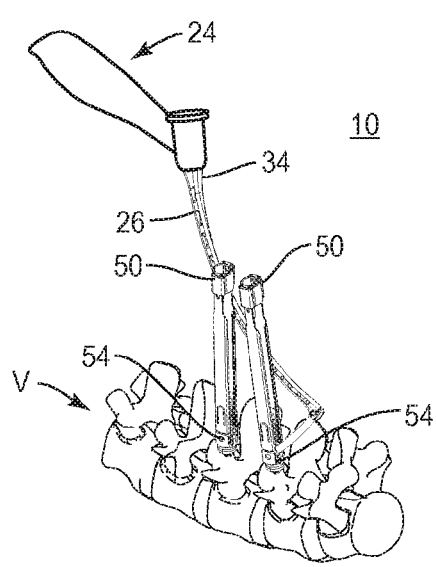
FIG. 3 is a perspective view of the components and vertebrae shown in FIG. 1.

Instrument 12 is manipulated such that sleeve 26 is disposed adjacent rails 42, 44, as shown in FIGS. 2-3. Extenders 40 include caps 50 such that sleeve 26 is disposed outside of rails 42, 44. Sleeve 26 is substantially prevented from entering passageway 52. Sleeve 26 is oriented such that spinal rod 14 enters passageway 52.

Figure 4:
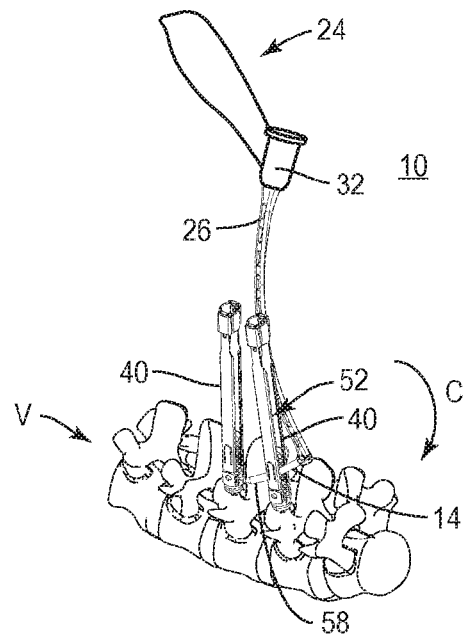
FIG. 4 is a perspective view of the components and vertebrae shown in FIG. 1.
Figure 5:
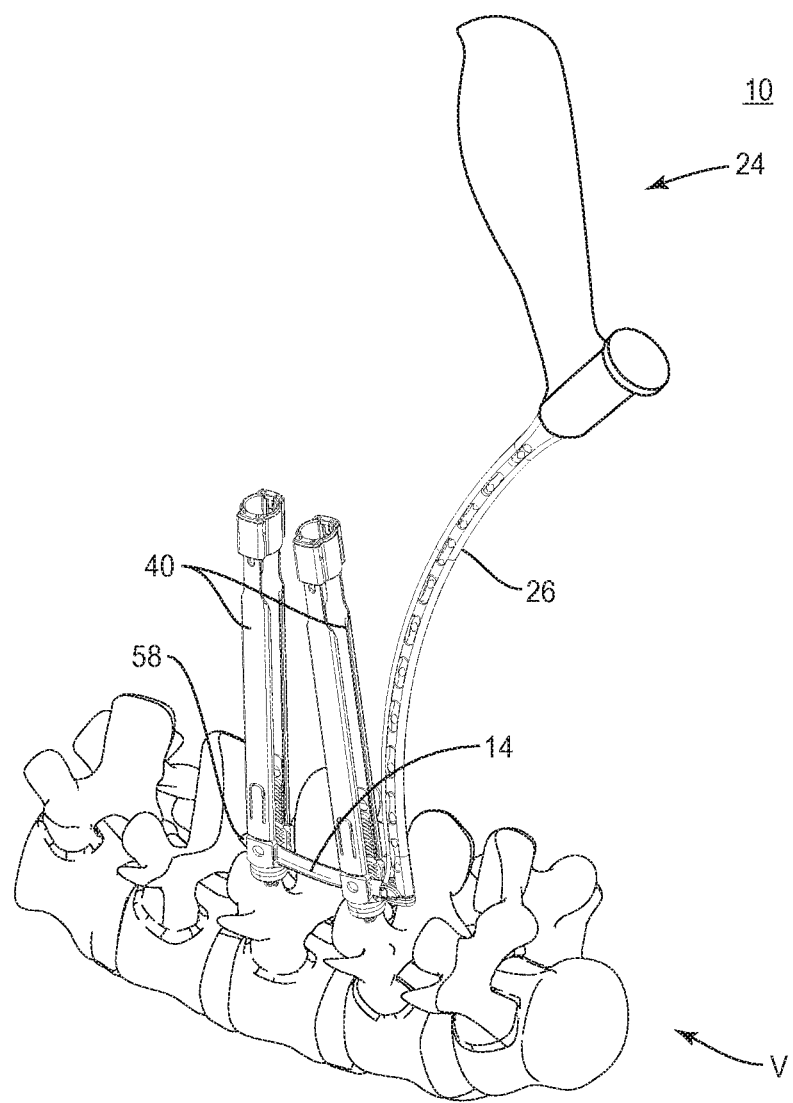
FIG. 5 is a perspective view of the components and vertebrae shown in FIG. 1.

Handle 24 is manipulated to rotate sleeve 26 and spinal rod 14, in the direction shown by arrow C in FIG. 4, to guide spinal rod 14 through passageway 52. Spinal rod 14 is rotated into implant cavities 46 of pedicle screws 54, as shown in FIG. 5. Once spinal rod 14 is disposed within implant cavities 46, spinal rods 14 are locked with pedicle screws 54 by coupling members, such as, for example, set screws. Knob portion 32 is rotated in a clockwise direction such that jaws 22, 38 are moved to a non-locking orientation to disengage and/or release spinal rod 14 from instrument 12. In some embodiments, instrument 12 and/or the non-implanted components of system 10 are removed from the surgical site and the incision is closed.

In one embodiment, as shown in FIGS. 6-10, similar to the assembly, operation and use described with regard to FIGS.

1-5, system 10, similar to that described above, includes extenders 40 each having proximal ends 47 that each define openings 56.

Figure 6:
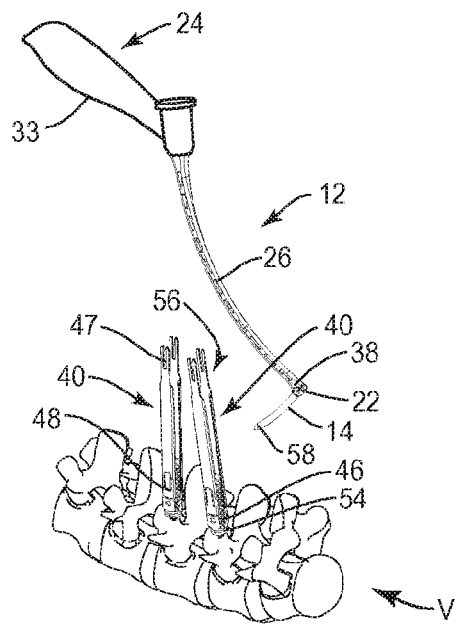
FIG. 6 is a perspective view of components of one embodiment of a surgical implant system in accordance with the principles of the present disclosure disposed with vertebrae.

Jaws 22, 38 are disposed adjacent spinal rod 14 and in a non-locking and open orientation. Knob portion 32 is rotated such that jaws 22, 38 move to a locking and closed orientation to capture spinal rod 14, as described. Pedicle screws 54 are delivered via the stab incision and fastened with vertebrae V, as described. Spinal rod 14 is delivered through the stab incision inclined relative to the extenders 40 along the pathway, as shown in FIG. 6. Handle 24 is manipulated such that sleeve 26 is disposed transverse to extenders 40 and spaced above extenders 40. Spinal rod 14 is inclined relative to the extenders 40 and a distal end 58 of spinal rod 14 is oriented in a direction towards vertebrae V.

Figure 7:
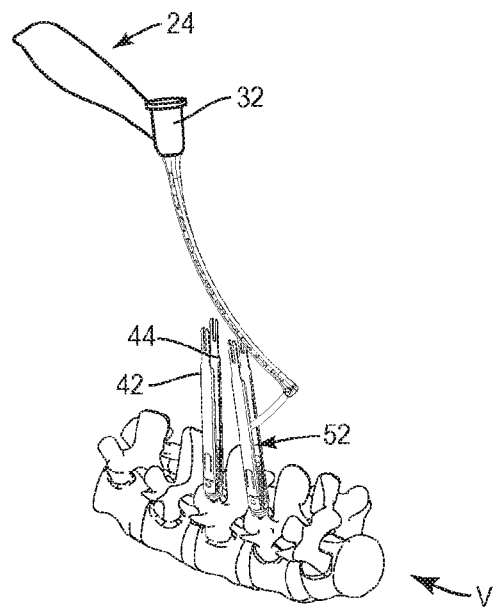
FIG. 7 is a perspective view of the components and vertebrae shown in FIG. 6.
Figure 8:
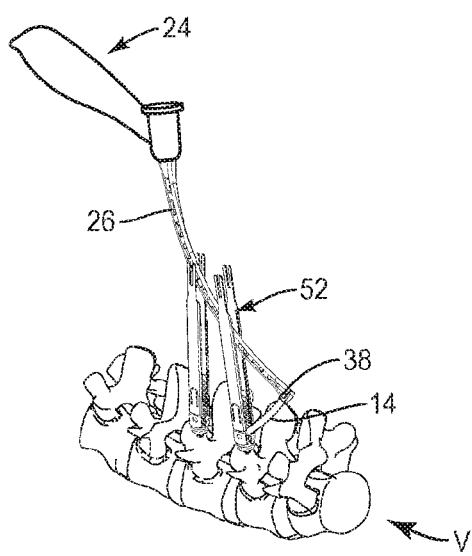
FIG. 8 is a perspective view of the components and vertebrae shown in FIG. 6.

Instrument 12 is manipulated such that sleeve 26 is disposed between rails 42, 44 and within passageways 52 of each extender 40, as shown in FIGS. 7 and 8. Sleeve 26 passes through openings 56 and into passageways 52 such that sleeve 26 is disposed inside of rails 42, 44. Sleeve 26 is oriented such that spinal rod 14 enters passageway 52 and is moved adjacent pedicle screws 54.

Figure 9:
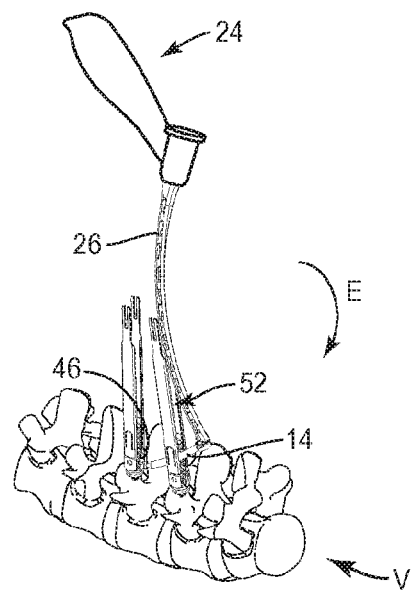
FIG. 9 is a perspective view of the components and vertebrae shown in FIG. 6.
Figure 10:
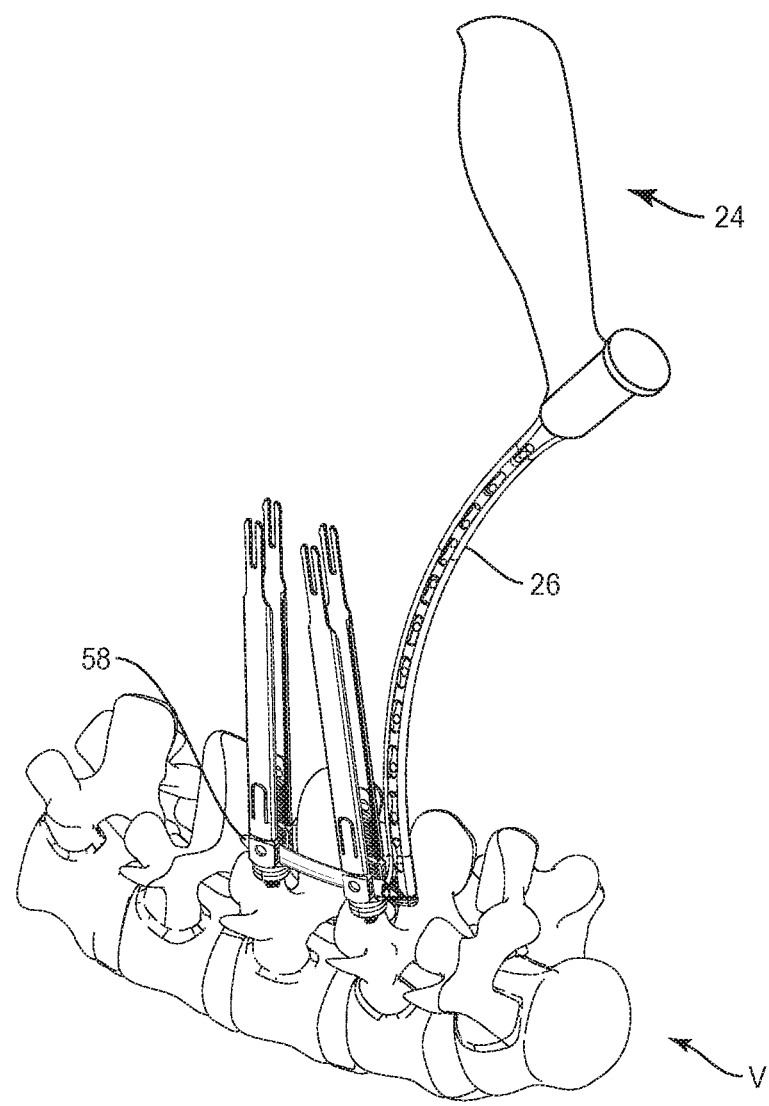
FIG. 10 is a perspective view of the components and vertebrae shown in FIG. 6.

Handle 24 is manipulated to rotate sleeve 26 and spinal rod 14, in the direction shown by arrow E in FIG. 9, to guide spinal rod 14 through passageway 52. Spinal rod 14 is rotated into implant cavities 46 of pedicle screws 54, as shown in FIG. 10. Once spinal rod 14 is disposed within implant cavities 46, spinal rods 14 are locked with pedicle screws 54 by set screws. Knob portion 32 is rotated in a clockwise direction such that jaws 22, 38 are moved to a non-locking orientation to disengage and/or release spinal rod 14 from instrument 12. In some embodiments, instrument 12 and/or the non-implanted components of system 10 are removed from the surgical site and the incision is closed.

One or more of the components of system 10 can be made of radiolucent materials such as polymers. Radiomarkers may be included for identification under x-ray, fluoroscopy, CT or other imaging techniques. In some embodiments, the use of microsurgical and image guided technologies may be employed to access, view and repair spinal deterioration or damage, with the aid of system 10.

In some embodiments, system 10 may include one or a plurality of spinal rods and/or bone fasteners for use with a single vertebral level or a plurality of vertebral levels. In some embodiments, the rods and/or bone fasteners may be engaged with vertebrae in various orientations, such as, for example, series, parallel, offset, staggered and/or alternate vertebral levels. In some embodiments, the bone fasteners may include one or a plurality of multi-axial screws, sagittal angulation screws, pedicle screws, mono-axial screws, uni-planar screws, fixed screws, tissue penetrating screws, conventional screws, expanding screws, anchors, buttons, connectors, clips, snaps, friction fittings, compressive fittings, expanding rivets, staples, nails, adhesives, fixation plates and/or posts. The rods and/or bone fasteners may be coated with an osteoinductive or osteoconductive material to enhance fixation, and/or include one or a plurality of therapeutic agents.

In one embodiment, system 10 includes an agent, which may be disposed, packed, coated or layered within, on or about the components and/or surfaces of system 10. In some embodiments, the agent may include bone growth promoting material, such as, for example, bone graft to enhance fixation of the fixation elements with vertebrae. In some embodiments, the agent may include one or a plurality of therapeutic agents and/or pharmacological agents for release, including sustained release, to treat, for example, pain, inflammation and degeneration.

In some embodiments, system 10 may include one or a plurality of inserters, extenders, reducers, bone fasteners, rods and/or other vertebral constructs, which may be alternately sized and dimensioned, and arranged as a kit, according to the requirements of a particular application.

Figure 11:
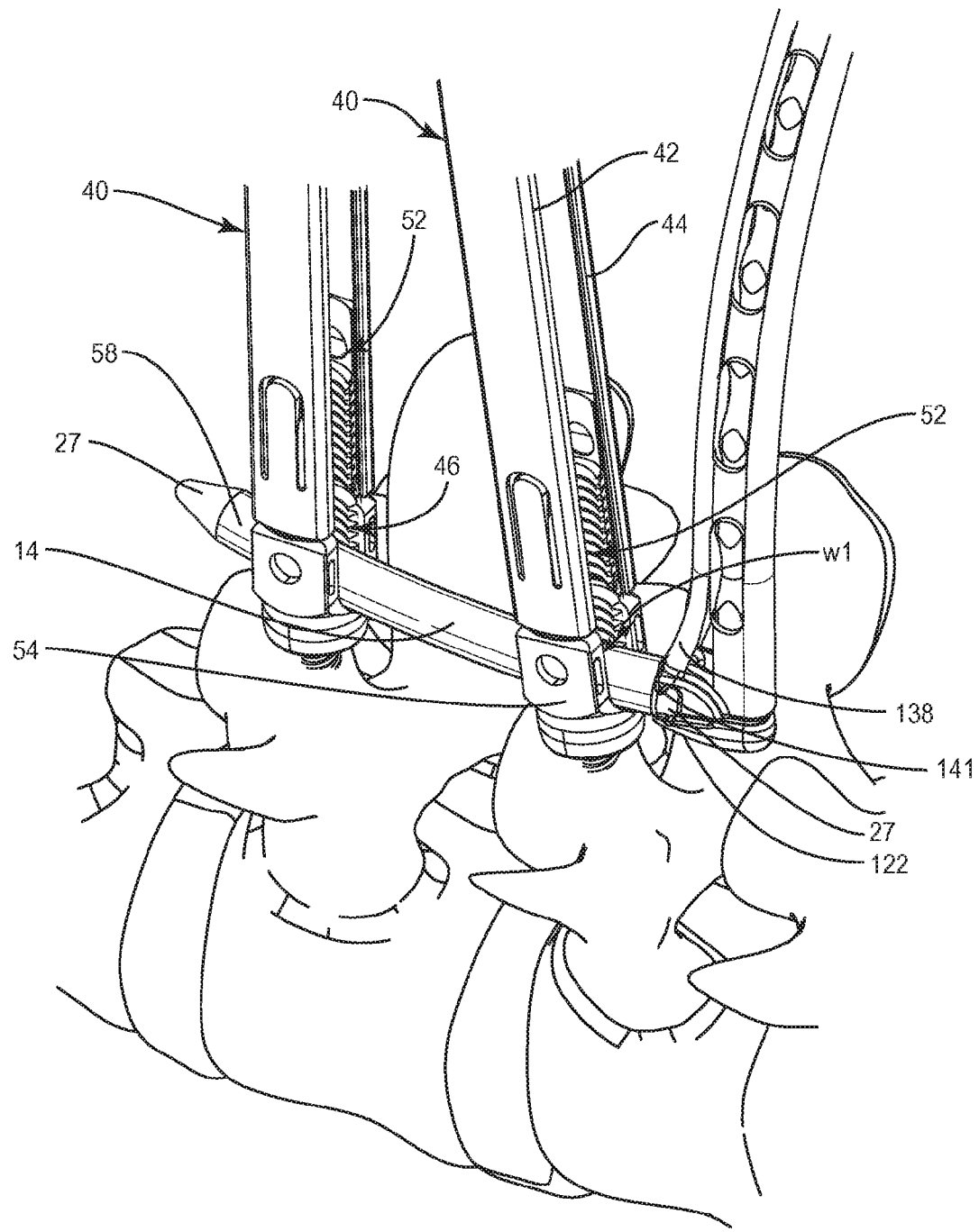
FIG. 11 is a break away, perspective view of components of one embodiment of a surgical implant system in accordance with the principles of the present disclosure.
Figure 12:
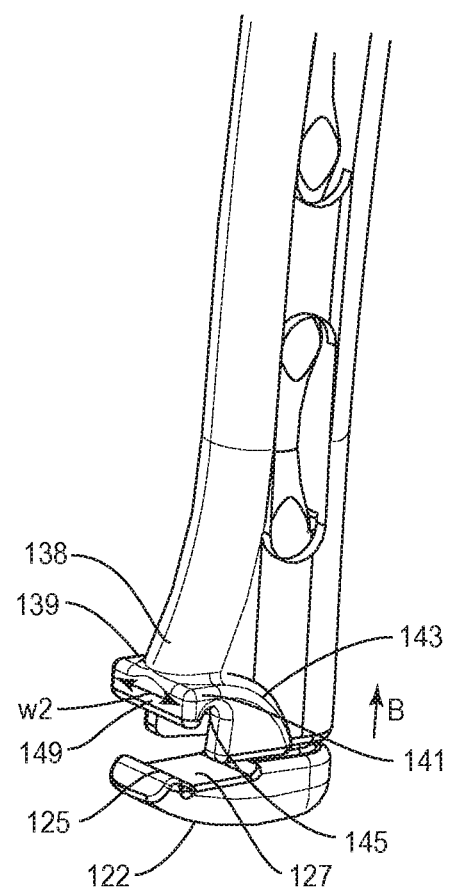
FIG. 12 is an enlarged break away view of components shown in FIG. 11.
Figure 13:
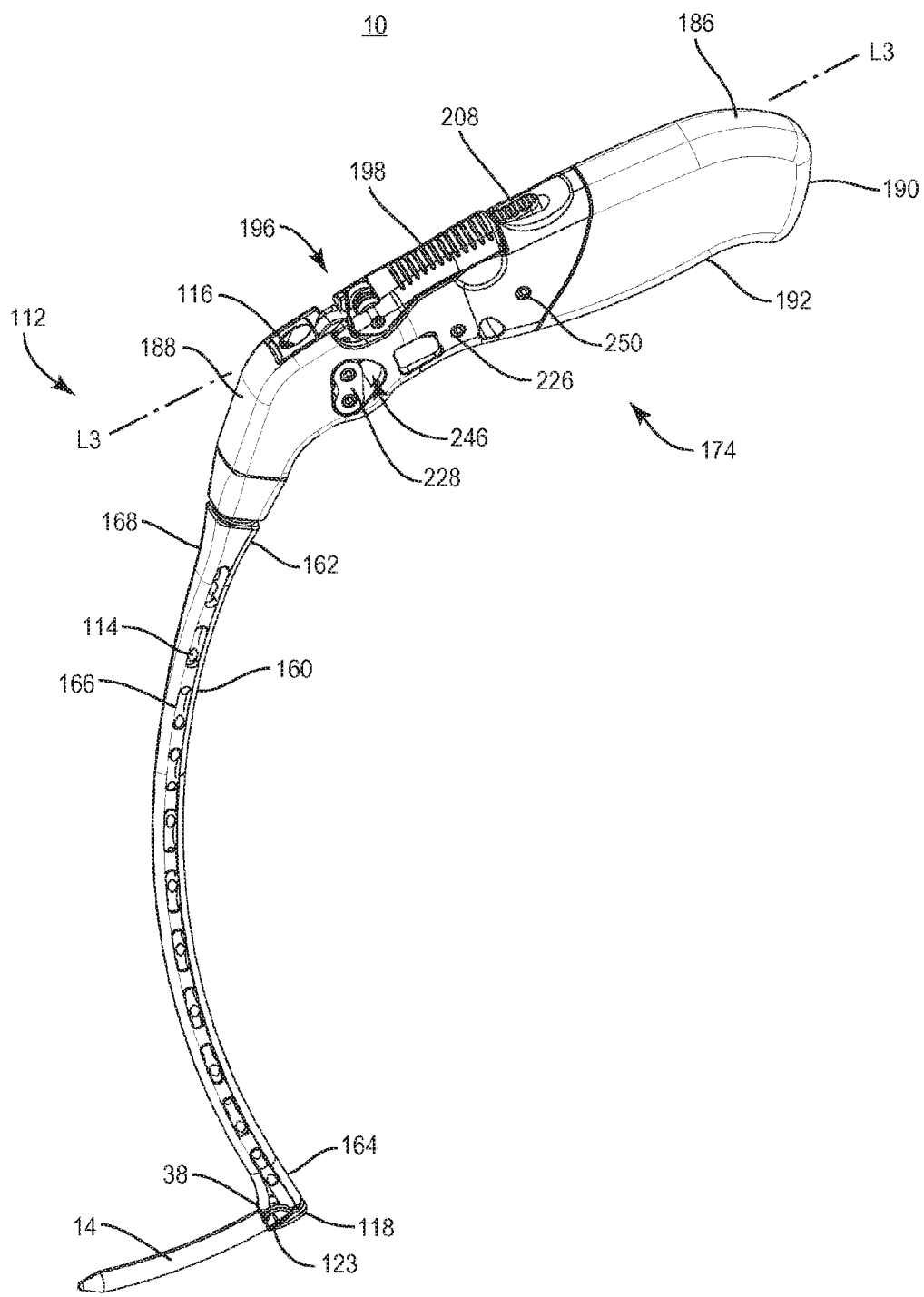
FIG. 13 is a perspective view of components of one embodiment of a surgical implant system in accordance with the principles of the present disclosure.
Figure 14:
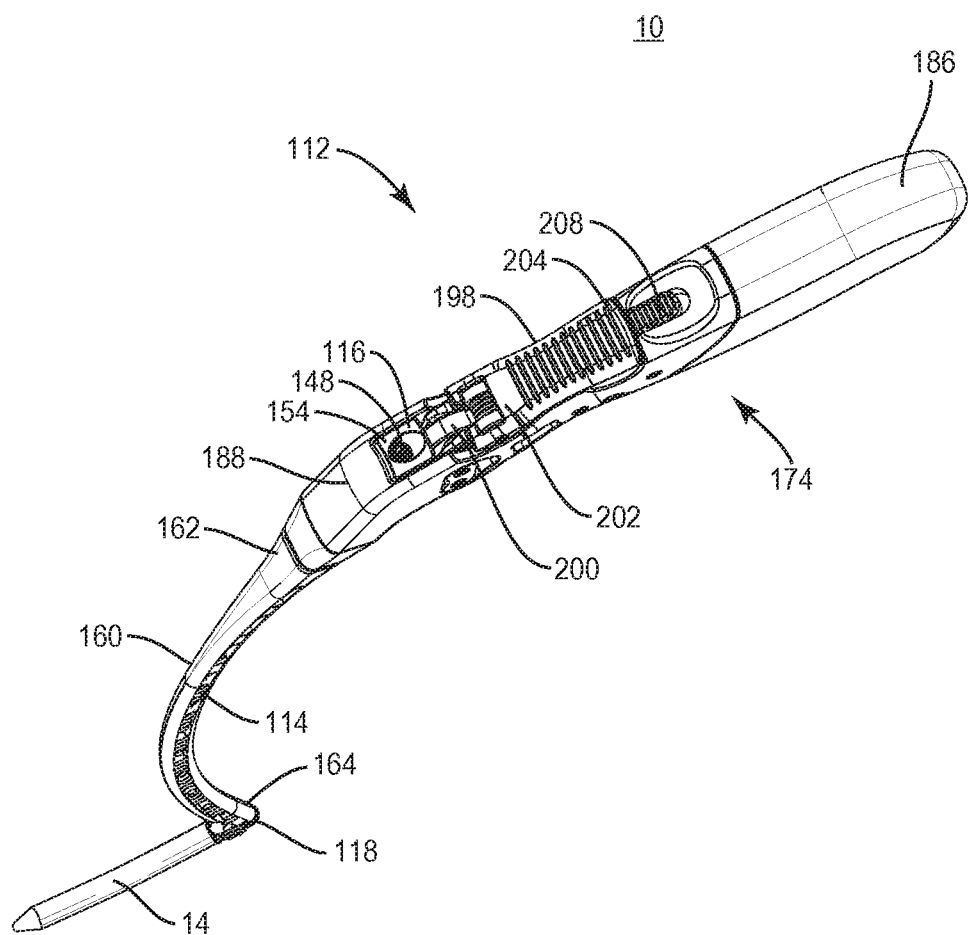
FIG. 14 is a perspective view of the components shown in FIG. 13.

In one embodiment, as shown in FIGS. 11 and 12, system 10, similar to the systems and methods described above with regard to FIGS. 1-10, comprises instrument 12 including the inner shaft, described above, which has a jaw 122, similar to jaw 22 described above. Jaw 122 includes an inner surface 127 defining a groove 125 configured for mating engagement with a cone 27 of spinal rod 14. Sleeve 26, described above, includes a jaw 138, similar to jaw 38 described above. The inner shaft translates within and relative to sleeve 26 causing jaw 122 of the inner shaft to move adjacent and/or engage jaw 138 to capture spinal rod 14 and/or space from jaw 138 to release spinal rod 14.

Jaw 138 includes embossed surfaces, such as, for example, bosses 139, 141. Bosses 139, 141 extend laterally from jaw 138 such that jaw 138 has a width dimension w2. Width dimension w2 is greater than width dimension w1 of implant cavities 46. Bosses 139, 141 each include an arcuate surface 143 and a slot 145 configured for mating engagement with cone 27. Bosses 139, 141 each define a substantially rectangular planar face 149 configured for engagement with rails 42, 44 of extenders 40.

Width dimension w2 of jaw 138 is dimensioned such that jaw 138 is configured to resist and/or is prevented from entering within implant cavities 46 of extenders 40 such that, for example, spinal rod 14 can be selectively disposed within passageway 52 at a selected depth between rails 42, 44. In some embodiments, this configuration facilitates guiding spinal rod 14, captured with jaws 122, 138, to the surgical site, for example, for disposal with implant cavities 46.

In one embodiment, as shown in FIGS. 13-25, system 10, similar to the systems and methods described above with reference to FIGS. 1-10, comprises an instrument 112, similar to instrument 12 described above. Instrument 112 includes a first member, such as, for example, an inner shaft 114 extending between an end 116 and an end 118. End 118 includes a clamp, such as, for example, a jaw 123, similar to the jaws described herein.

Figure 15:
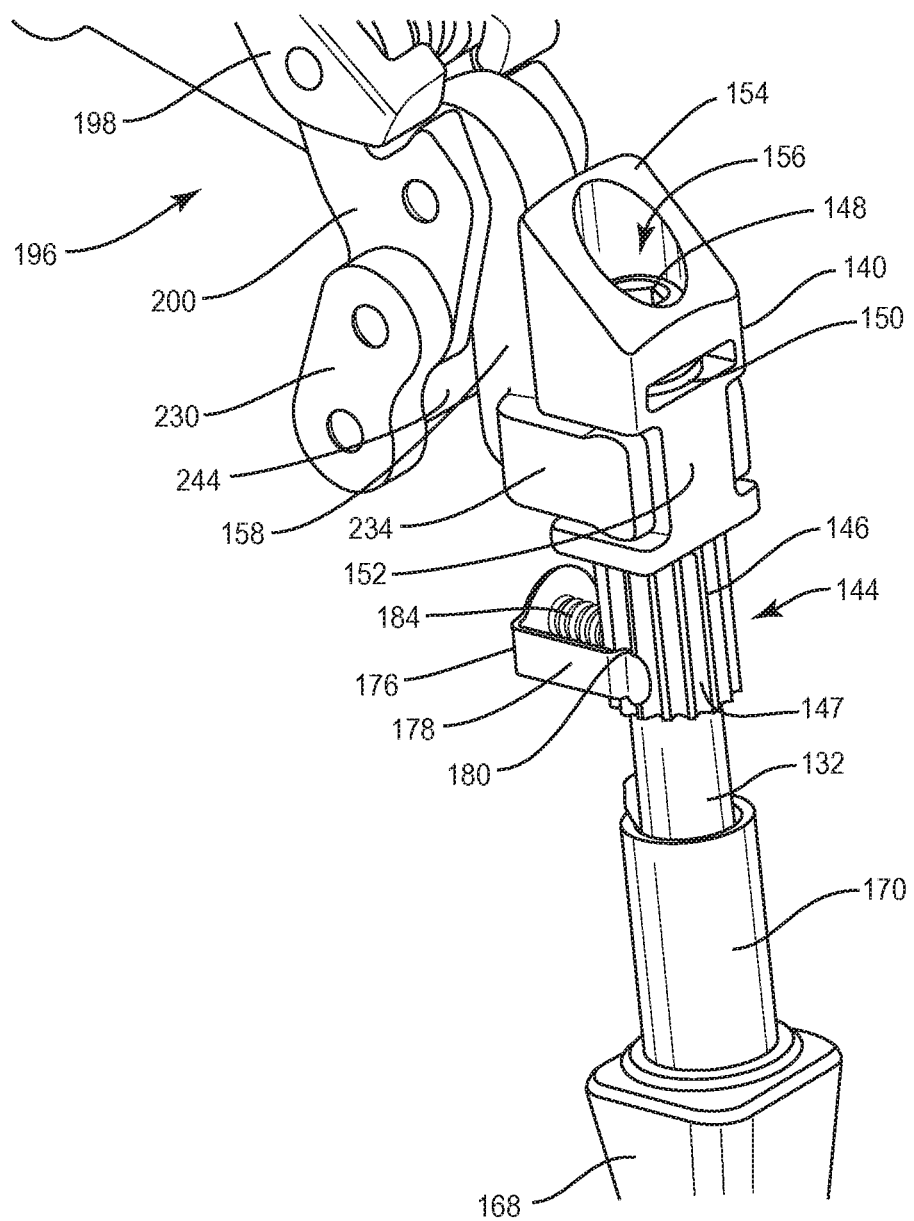
FIG. 15 is an enlarged cutaway view of the components shown in FIG. 13.
Figure 16:
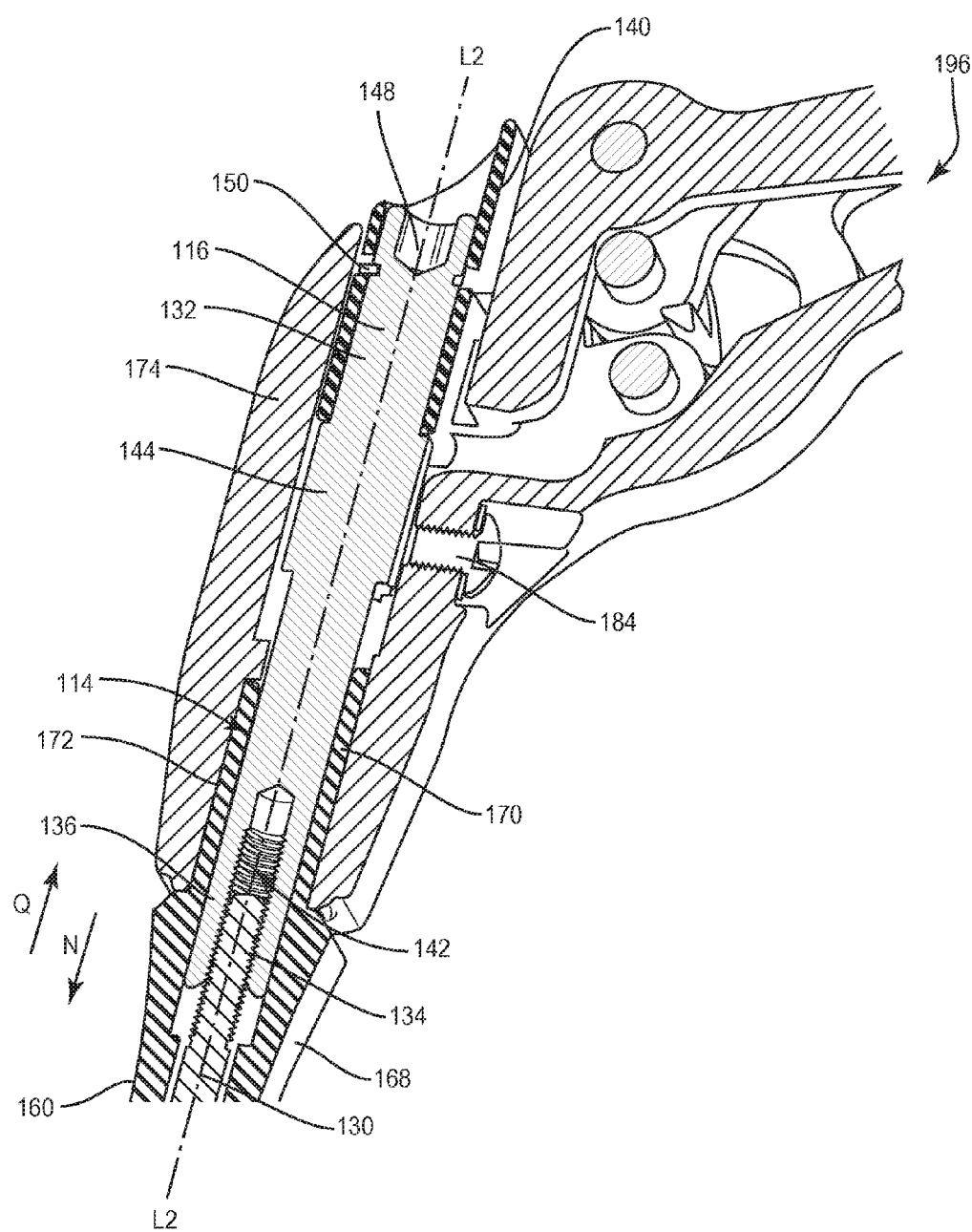
FIG. 16 is a side cross-sectional view of the components shown in FIG. 15.

Inner shaft 114 includes a first shaft, such as, for example, a rod inserter clamp shaft 130 and a second shaft, such as, for example, a latch pull shaft 132 configured for threaded engagement with shaft 130, as shown in FIGS. 15 and 16. Shafts 130, 132 are relatively movable to relatively translate jaw 123 for tensioning engagement with a spinal construct, such as, for example, spinal rod 14, described herein.

Shaft 130 extends between end 118 and a proximal end, such as, for example, a proximally threaded portion 134. End 118 includes jaw 123. Proximally threaded portion 134 is threadedly engaged to a second end 136 of shaft 132. Shaft 130 is disposed within a cavity (not shown) defined by a second member, such as, for example, an outer sleeve 160. Shaft 130 is flexible and has a substantially arcuate cross-section configuration. In some embodiments, the cross-section of shaft 130 is variously configured, such as, for example, oval, rectangular, polygonal, irregular and/or tapered.

Shaft 132 extends between end 116 and end 136, which defines a longitudinal axis L2. End 136 includes a threaded cavity 142 configured for threaded engagement with proximally threaded portion 134. Cavity 142 has a substantially arcuate cross section configuration. In some embodiments, the cross section of cavity 142 is variously configured, such as, for example, oval, rectangular, polygonal, irregular and/or tapered. Shaft 132 has a varying thickness along axis L2. In some embodiments, the cross-section of shaft 132 is variously configured, such as, for example, those alternatives described herein.

Shaft 132 includes an intermediate section 144 disposed between ends 116, 136. Intermediate section 144 has a cylindrical configuration. In some embodiments, intermediate section 144 is variously configured, such as, for example, oval, rectangular, polygonal, irregular and/or tapered. Intermediate section 144 includes a gear surface 146 extending radially therefrom and defining teeth 147. Teeth 147 are configured for mating engagement with a leaf spring detent system, such as, for example, a detent lock 176.

Detent lock 176 is engageable with shaft 132 to prevent rotation of shaft 132. Detent lock 176 includes flanges 178 extending in a transverse orientation relative to shaft 132. Flange 178 includes a protrusion 180 configured for mating engagement with teeth 147. Detent lock 176 includes a fastener, such as, for example, a screw 184. Screw 184 is configured to be threaded with flanges 178 to unreleasably lock teeth 147.

Instrument 112 includes a second member, such as, for example, an outer sleeve 160, similar to sleeve 26 described herein. Sleeve 160 extends between a first end 162 and a second end 164. End 164 includes a clamp, such as, for example, a jaw 139, similar to the jaws described herein. Sleeve 160 defines a cavity configured for disposal of inner shaft 114. In some embodiments, sleeve 160 may have alternate cross section shapes, such as, for example, oval, circular, oblong, triangular, square, polygonal, irregular, uniform, non-uniform, offset, staggered, undulating, arcuate, variable and/or tapered depending on a particular application. Sleeve 160 has an arcuate curvature extending between ends 162, 164. Sleeve 160 includes a plurality of openings 166 to provide visualization of shaft 114 and cleaning.

Shaft 132 includes a socket 148 disposed at end 116. Socket 148 has a hexagonal configuration configured to engage a correspondingly shaped portion of a driving tool (not shown). In some embodiments, socket 148 may be variously configured, such as, for example, Phillips head, slotted head, hex socket head, hexagon external head, frearson head, square socket, square slotted combination head, spanner drilled tamper proof head and combinations thereof. Rotating socket 148 with a driving tool causes shaft 132 to rotate such that shaft 130 translates relative to shaft 132 to selectively tension the engagement of jaws 123, 139 with spinal rod 14 to selectively set the clamping force.

Shaft 132 includes a translation sleeve 140 disposed about end 116 of shaft 132. Translation sleeve 140 is coupled to shaft 132 by a fastening member, such as, for example, a c-clip 150. In some embodiments, translation sleeve 140 is fastened to shaft 132 in various ways, such as, for example, frictional engagement, threaded engagement, mutual grooves, screws, glue, nails, serrated, textured, staggered, uneven, undulating, smooth, barbs and/or raised element. Translation sleeve 140 is connected to a third member, such as, for example, an actuator 196. Translation sleeve 140 includes a rectangular body 152 configured for disposal about shaft 132. Translation sleeve 140 includes a tapered surface 154 shaped and dimensioned for disposal within a handle body 174. Translation sleeve 140 defines an opening 156 configured for disposal of end 116 of shaft 132 and socket 148.

Outer sleeve 160 includes a tapered portion 168 disposed at end 162. Tapered portion 168 provides a transition between sleeve 160 and a handle body 174. Tapered portion 168 includes a hollowed cylindrical extension 170, as shown in FIGS. 15-16, extending therefrom and configured for fixed engagement with an interior surface 172 of handle body 174, connecting sleeve 160 with handle body 174. Extension 170 is disposed about end 136 of shaft 132 such that extension 170 is disposed between handle body 174 and shaft 132. Extension 170 and/or interior surface 172 of handle body 174 may be rough, arcuate, undulating, porous, semi-porous, dimpled, polished and/or textured, to enhance engagement with one another. In some embodiments, all or only a portion of extension 170 may have alternate cross section configurations, such as, for example, oval, oblong, triangular, square, polygonal, irregular, uniform, non-uniform, offset, staggered, and/or tapered.

Handle body 174 extends between a first end 186 and a second end 188. End 186 includes an outer surface 190 that defines finger grooves 192 and defines an axis L3. End 188 includes detent lock 176 and defines a cavity (not shown) configured for disposal of at least a portion of inner shaft 114. In some embodiments, outer surface 190 may have various surface configurations, such as, for example, rough, threaded, arcuate, undulating, porous, semi-porous, dimpled, polished and/or textured, to enhance gripping of handle body 174.

Figure 19:
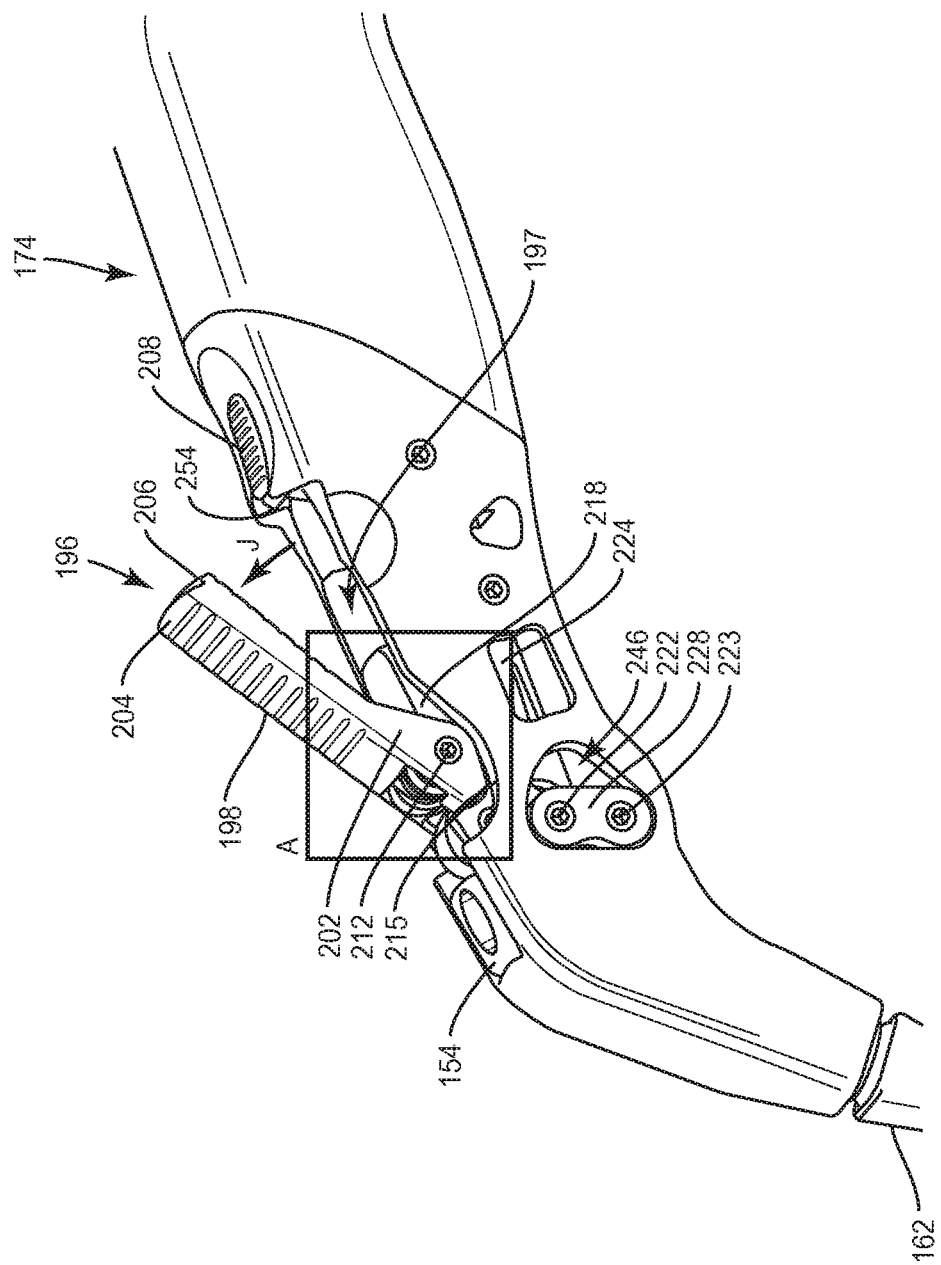
FIG. 19 is a break away view of the components shown in FIG. 13.
Figure 20:
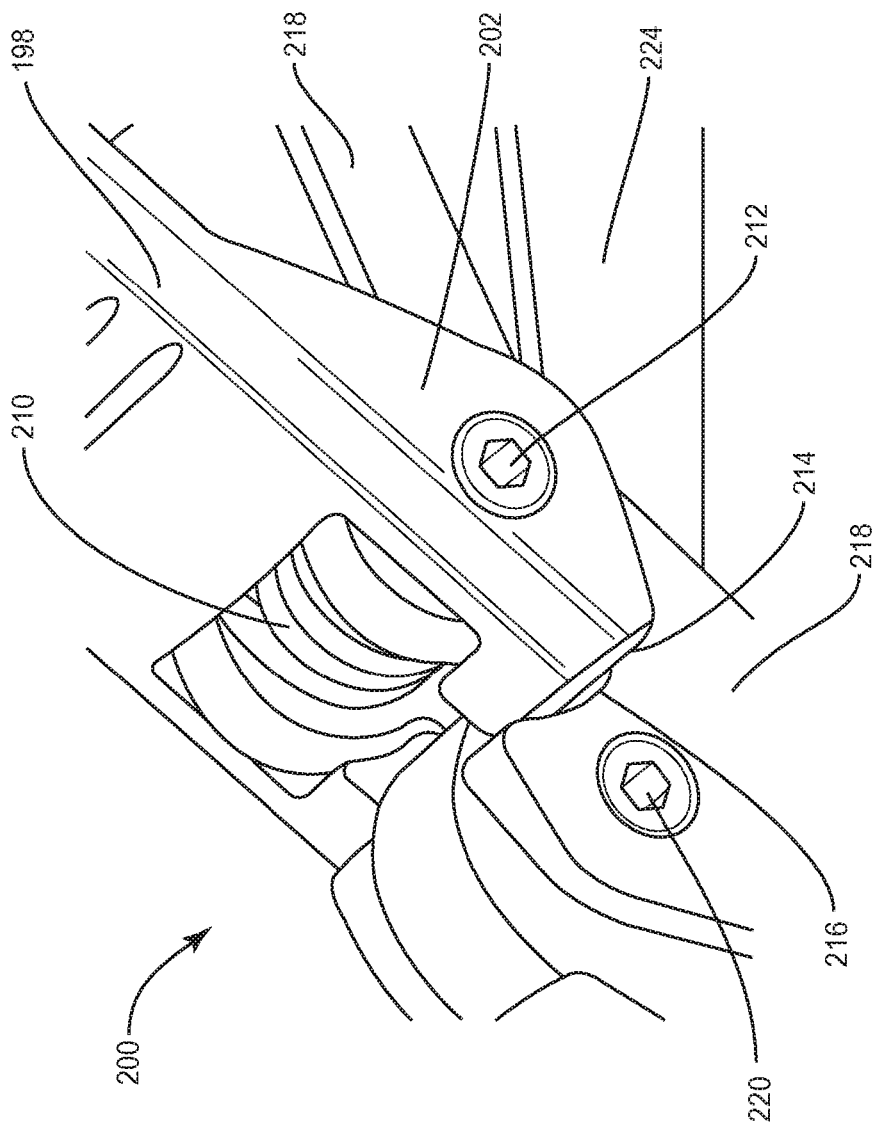
FIG. 20 is an enlarged view of detail A shown in FIG. 19.
Figure 21:
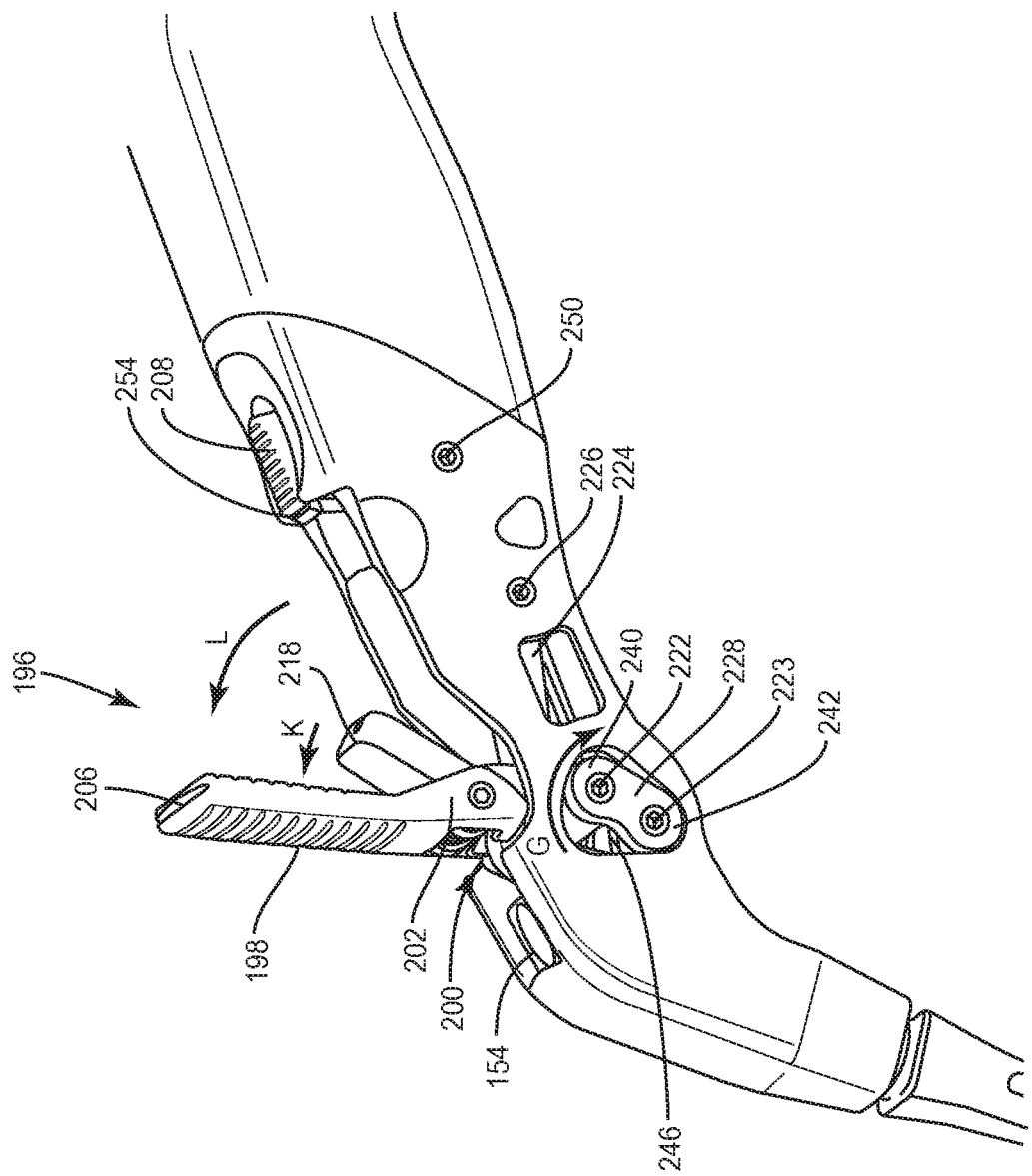
FIG. 21 is a break away view of the components shown in FIG. 13.

Handle body 174 defines a cavity 197, which is configured for disposal of actuator 196. Actuator 196 includes a part, such as, for example, a first lever or clamp lever 198 and a second lever, such as, for example, a main lever 200. Lever 198 includes a first end 202 and a second end 204 having a notch 206 matingly engageable with a latch lock release button 208, as shown in FIGS. 19-21. End 202 is pivotally connected to lever 200 about a pivot point 212. End 202 is shaped to engage a slot 216 of lever 200. Lever 198 engages the surface of slot 216 to dispose lever 198, in a second locking orientation, an example of which being described herein. Lever 198 is rotatable to overcome the engagement with the surface of slot 216 to dispose lever 198 in a non-locking orientation, an example of which being described herein. In some embodiments, the surface of slot 216 may be variously shaped, such as, for example, hexagonal, star, square, slotted, indented hexagon, cross and/or slotted. In some embodiments, lever 198 may have alternate shapes, such as, for example, oval, oblong, triangular, square, polygonal, irregular, uniform, non-uniform, offset, staggered, and/or tapered. In some embodiments, lever 198 may have various surface configurations, such as, for example, rough, threaded, arcuate, undulating, porous, semi-porous, dimpled, polished and/or textured, to enhance gripping of lever 198. In one embodiment, end 202 can include a cam surface 214 that engages a cam surface 215 of handle body 174 to facilitate leverage in overcoming the force of the overcenter cam, described herein, and disposing lever 198 in a non-locking orientation.

Lever 198 is resiliently biased for rotation relative to handle body 174 by a biasing member, such as, for example, a torsion spring 210. Spring 210 is disposed between levers 198, 200. Lever 198 is biased outwardly from lever 200 and is pivotable about pivot point 212.

Figure 22:
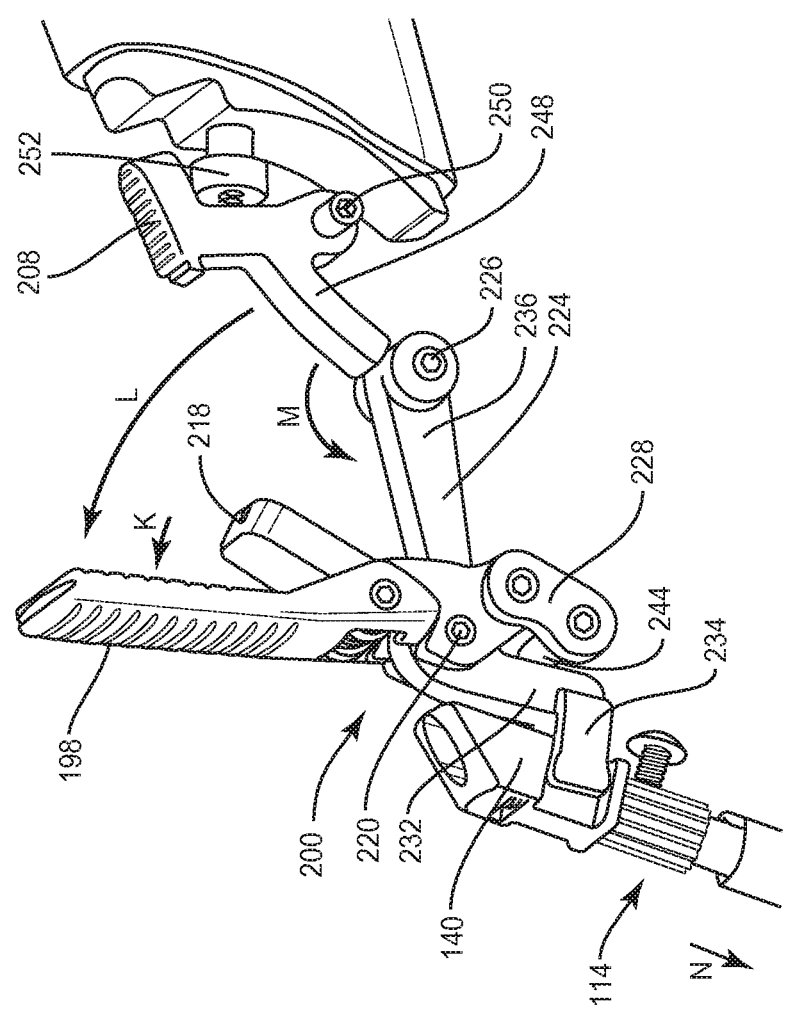
FIG. 22 is a cutaway view of the components shown in FIG. 21.

Lever 200 is connected to end 116 of inner shaft 114. Lever 200 includes a main clamp lever 218 and a cam linkage 224, as shown in FIG. 22. Main clamp lever 218 is pivotally linked to lever 198 at pivot point 212. Cam linkage 224 is pivotally linked to main clamp lever 218 at a pivot point 220. Cam linkage 224 includes a first end 232 and a second end 236. End 232 includes a coupler, such as, for example, a c-clip 234, which comprises flanges 178, connected to translation sleeve 140. End 236 is pivotally engagable with handle body 174 at a pivot point 226. In some embodiments, cam linkage 224 is coupled to translation sleeve 140 in various ways, such as, for example, a hook, clip, rod, tab, detent and/or key.

Actuator 196 includes over center cams 228, 230 each having a first end 240 and a second end 242. End 240 is pivotally connected to main clamp lever 218 at a pivot point 222. End 242 is pivotally connected to a bar 244 at a pivot point 223, rotatably connecting cams 228, 230 to one another. Bar 244 is disposed in a substantially perpendicular orientation relative to cams 228, 230. Cams 228, 230 are disposed within openings 246 of handle body 174 such that cams 228, 230 are translatable within openings 246, in the direction shown by arrow G in FIGS. 17, 21 and 24, during actuation of actuator 196. Openings 246 include a first surface 247, a second surface 249, and a slot 251. Surfaces 247, 249 are configured to limit movement of cams 228, 230 within openings 246. End 242 is disposed within slot 251 such that end 240 of cams 228, 230 is rotatable between surfaces 247, 249 about pivot point 223 during actuation of actuator 196. In some embodiments, cams 228, 230 can be alternatively shaped, such as, for example, round, oval, oblong, triangular, polygonal having planar or arcuate side portions, irregular, uniform, non-uniform, consistent, variable, horseshoe shape, or U-shape.

Actuator 196 includes a locking element, such as, for example, latch lock release button 208. Button 208 is resiliently biased to detachably engage lever 198. Button 208 includes an extension member 248 pivotally coupled to handle body 174 at a pivot point 250. Member 248 is engageable with end 236 of cam linkage 224 limiting the rotation of member 248 about pivot point 250. Button 208 includes a biasing member 252 attached to handle body 174 and disposed adjacent to button 208 such that button 208 is resiliently biased to a locking orientation, such as, for example, those described herein. Button 208 further includes a notch 254 configured for detachable mating engagement with notch 206 of lever 198. In some embodiments, notch 254 is variously configured, such as for example, a hook, clip, rod, tab, detent and/or key.

Figure 17:
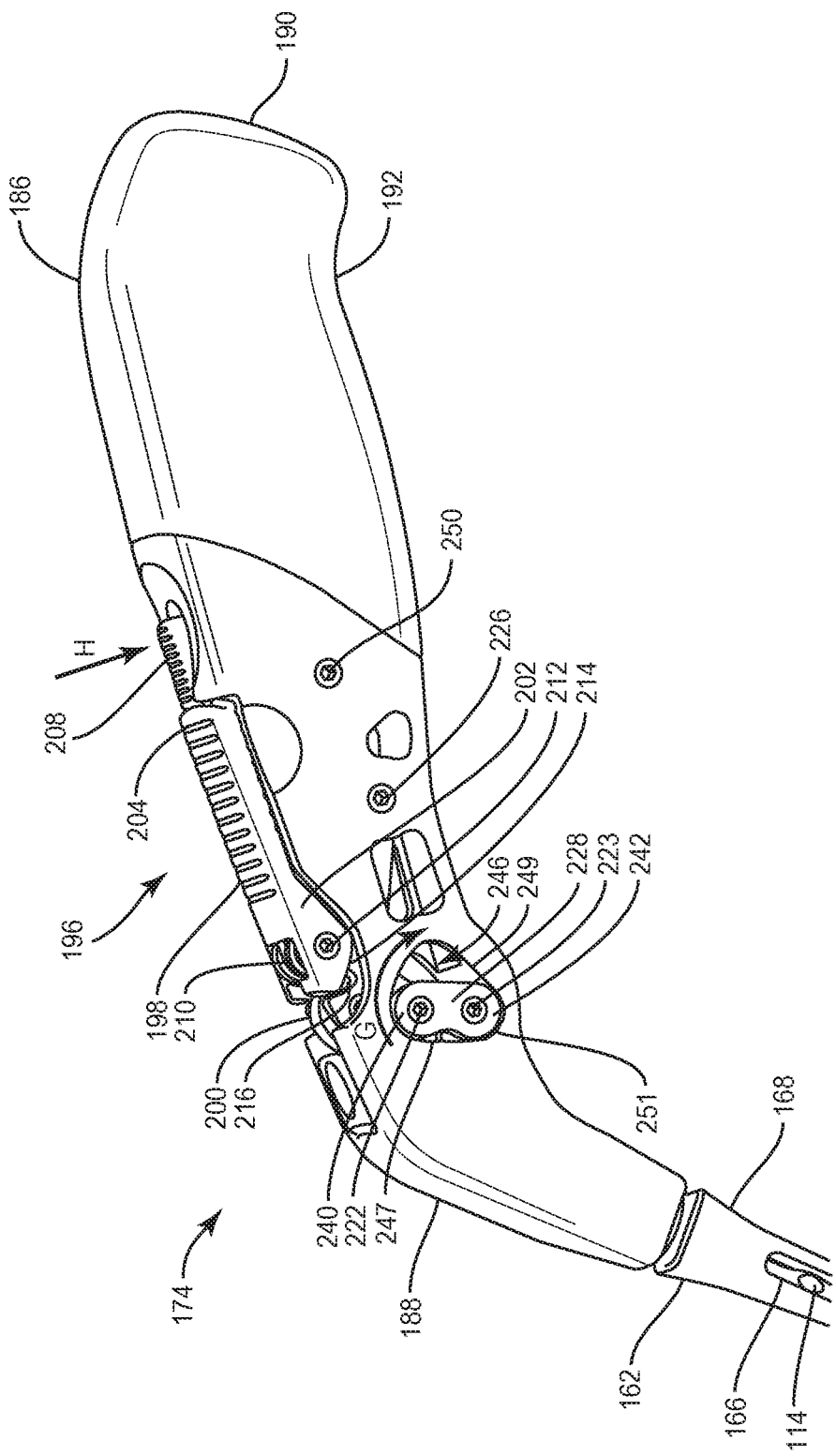
FIG. 17 is a break away view of the components shown in FIG. 13.
Figure 18:
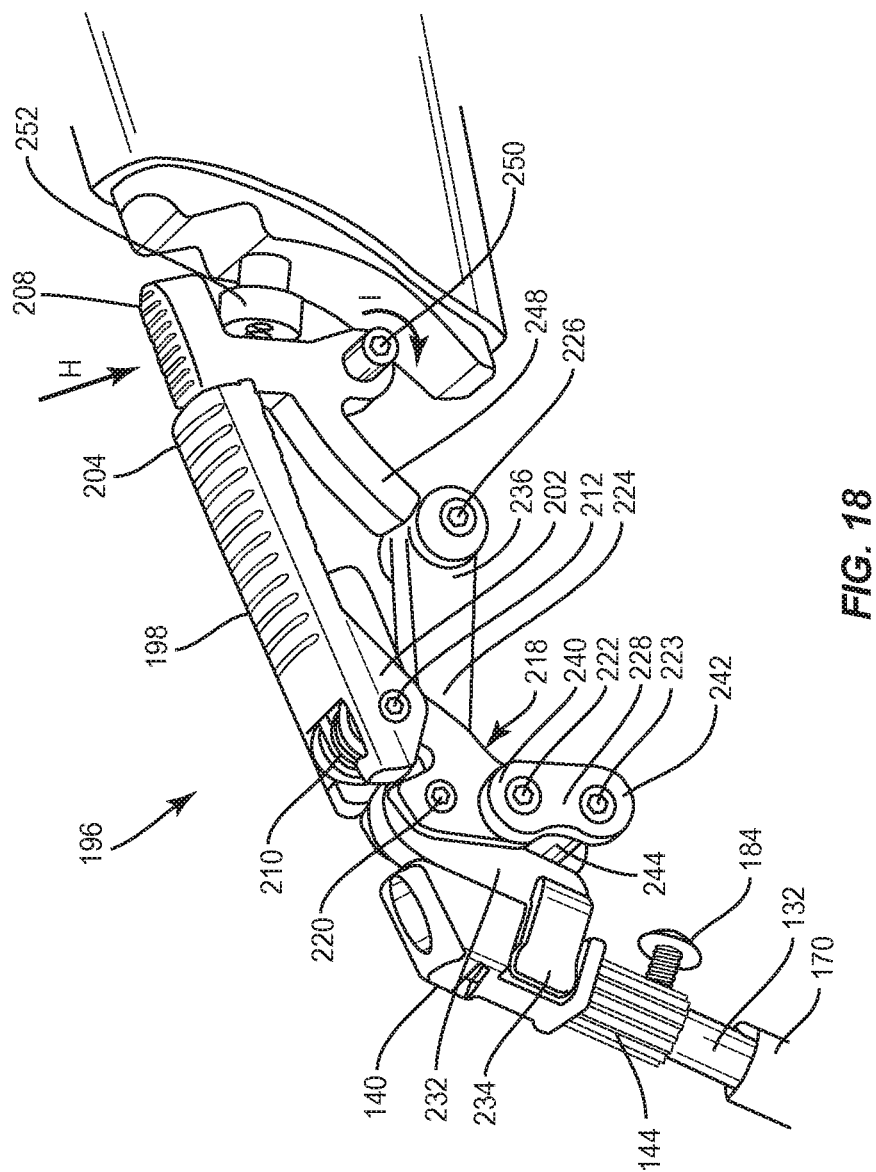
FIG. 18 is a cutaway view of the components shown in FIG. 17.

In operation, instrument 112 is selectively movable between a non-locking orientation, as shown in FIG. 21, and one or a plurality of locking orientations, as shown in FIGS. 17-20, to provide a practitioner with an improved grip on levers 198, 200 to, for example, overcome over tightening. In a first locking orientation, lever 198 is engaged to button 208 and jaws 123, 139 are disposed in a capturing engagement with spinal rod 14 at a selected tension, as shown in FIGS. 17 and 18.

To release spinal rod 14 from jaws 123, 139, a force, in the direction shown by arrow H in FIG. 18, is applied to button 208 causing biasing member 252 to compress. The compression of biasing member 252 allows extension member 248 to rotate, in the direction shown by arrow I, about pivot point 250 to disengage notch 206 of lever 198 from notch 254 of button 208. After button 208 and lever 198 are disengaged, spring 210 causes lever 198 to rotate, in the direction shown by arrow J in FIG. 19, relative to axis L3 and main clamp lever 218. Lever 198 rotates until edge 214 of lever 198 engages slot 216, as shown in FIG. 20, such that lever 198 is disposed in the second locking orientation, as shown in FIG. 19.

In the second locking orientation, the orientation of lever 198 relative to handle body 174 provides a practitioner more purchase on lever 198 to overcome the resistance to rotation of cams 228, 230. Main clamp lever 218 remains disposed in a locking orientation during the rotation of lever 198 from the first locking orientation to the second locking orientation. Cams 228, 230 remain engaged to surface 247 of opening 246 during rotation of lever 198 from the first locking orientation to the second locking orientation.

Figure 23:
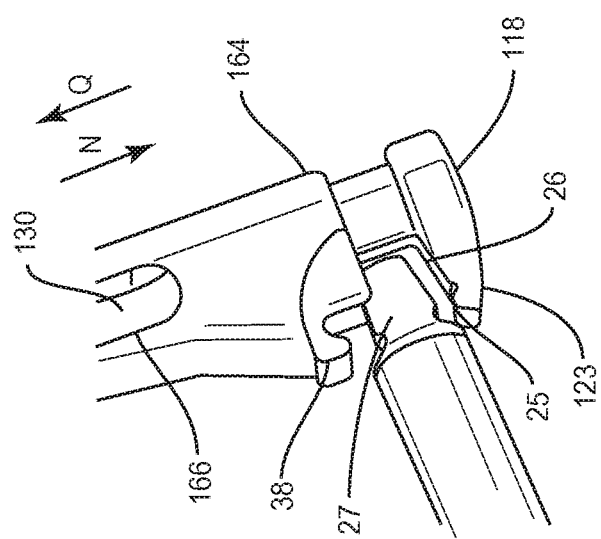
FIG. 23 is an enlarged break away view of the components shown in FIG. 13.
Figure 24:
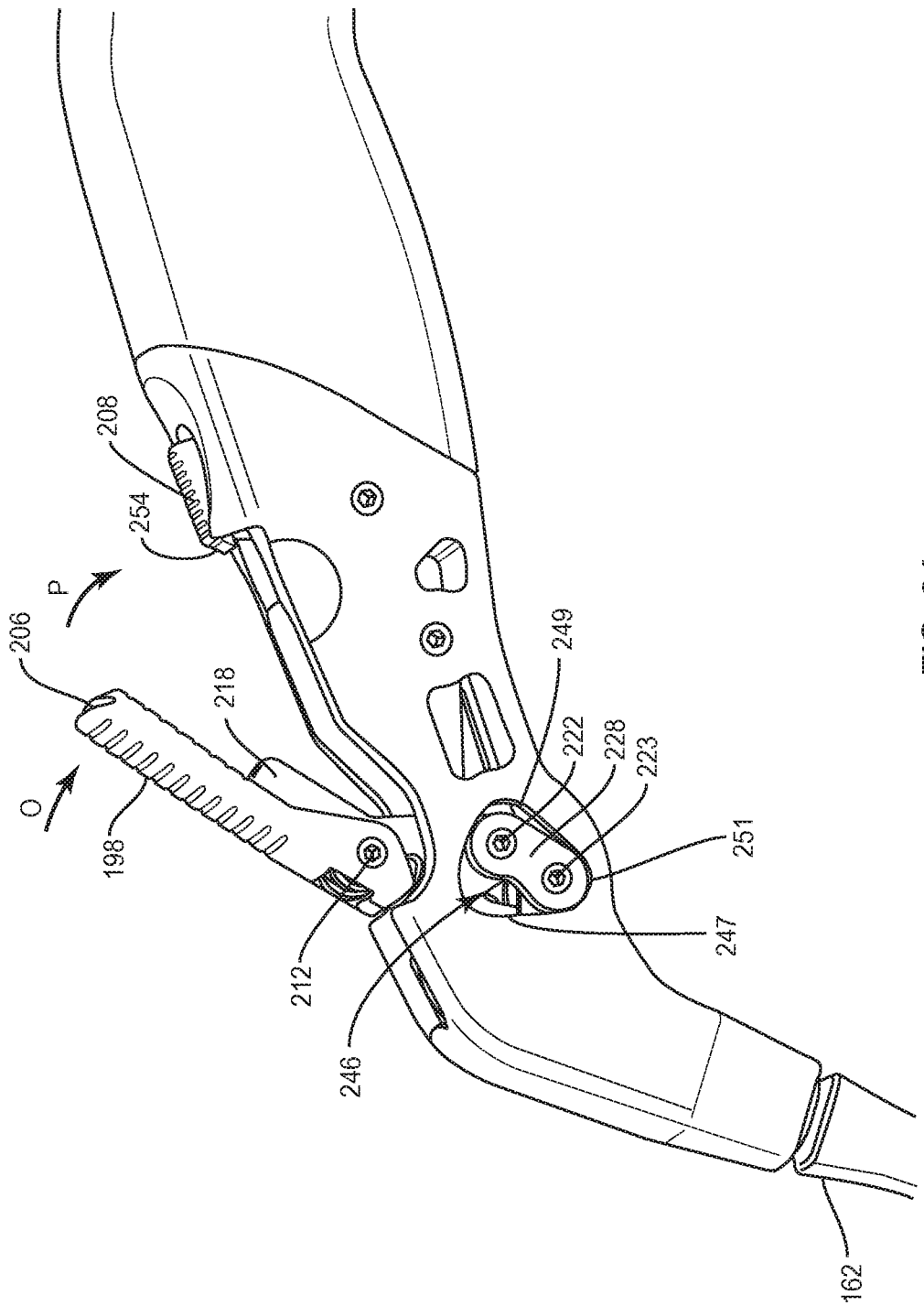
FIG. 24 is a break away view of the components shown in FIG. 13.
Figure 25:
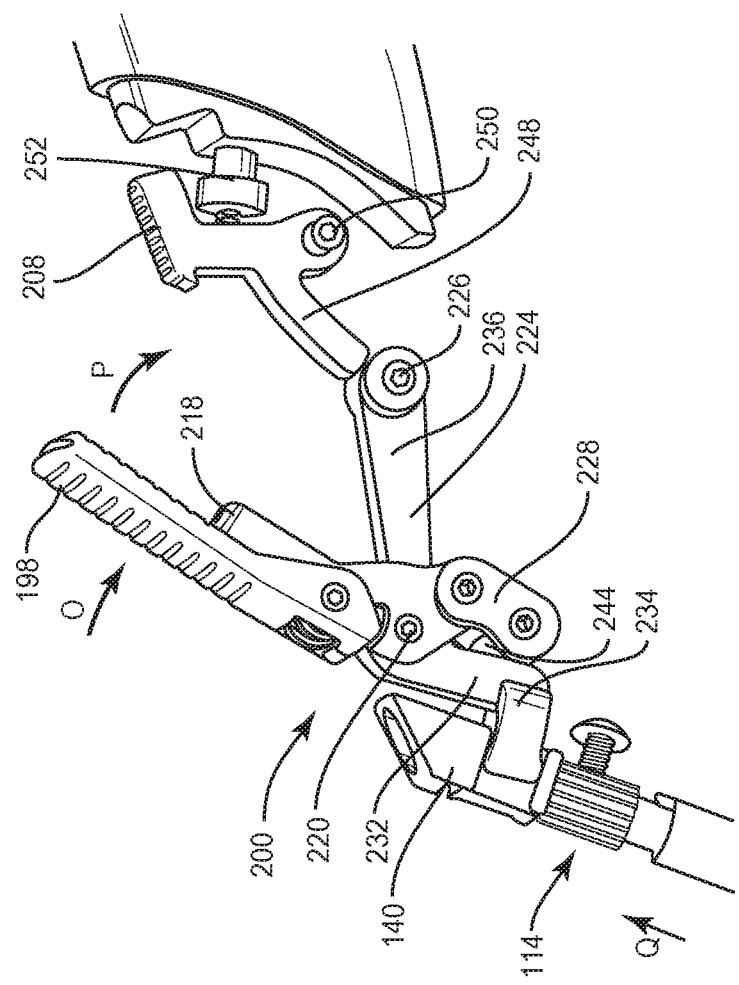
FIG. 25 is a cutaway view of the components shown in FIG. 24.

To dispose instrument 112 in a non-locking orientation, as shown in FIGS. 21-23, a force is applied to lever 198, in the direction shown by arrow K, which causes lever 218 to rotate, in the direction shown by arrow L, about pivot point 220 relative to cam linkage 224. Rotation of lever 218 causes rotation of cams 228, 230, in the direction shown by arrow G, within openings 246. Cams 228, 230 rotate about pivot point 223 to translate from surface 247 to engage surface 249 of handle body 174. Surface 249 prevents further rotation of cams 228, 230 about pivot point 223. Cams 228, 230 cause lever 218 to leverage the rotation of cam linkage 224, in the direction shown by arrow M in FIG. 22, about pivot point 226 to dispose levers 198, 218 in a non-locking orientation. End 236 of cam linkage 224 rotates about pivot point 226 causing end 232 of cam linkage 224 to translate axially, causing c-clip 234 to translate axially. Axial translation of c-clip 234 causes the axial translation of translation sleeve 140 and inner shaft 114, in the direction shown by arrow N in FIGS. 22 and 23, relative to handle body 174 and sleeve 160. Axial translation of inner shaft 114 causes jaw 123 to separate from jaw 139 to release spinal rod 14 from capture.

From the non-locking orientation, levers 198, 200 can be rotated such that instrument 112 is disposable in a second locking orientation and/or a first locking orientation, for example, such that jaws 123, 139 engage and capture spinal rod 14. From the non-locking orientation, a force is applied to lever 198, in the direction shown by arrow O in FIGS. 24 and 25, causing lever 198 to rotate, in the direction shown by arrow P, relative to lever 218 about pivot point 212 until levers 198, 218 are engaged in a substantially parallel alignment. Levers 198, 200 rotate, in the direction shown by arrow O, such that notch 206 engages notch 254 causing cams 228, 230 to engage surface 247. Inner shaft 114 is caused to translate, in the direction shown by arrow Q in FIG. 25, such that jaws 123, 139 capture spinal rod 14 and dispose instrument 112 in the first locking orientation.

In one embodiment, the tension of the engagement of jaws 123, 139 with spinal rod 14 is selectively adjustable to increase or decrease such tension. A driving tool (not shown) is inserted within socket 148 and rotated, for example, in a clockwise direction, such that shaft 132 rotates in a clockwise direction about proximally threaded portion 134 of shaft 130. The rotation of shaft 132 causes shaft 130 to translate axially, in the direction shown by arrow Q in FIGS. 16 and 25, relative to shaft 132, to increase the tension of the engagement of jaws 123, 139 with spinal rod 14. Shaft 130 is rotated, for example, in a counter clockwise direction, such that shaft 132 rotates in a counter clockwise direction about proximally threaded portion 134 to translate shaft 130 in a direction opposite to arrow Q, relative to shaft 132, to decrease the tension of the engagement of jaws 123, 139 with spinal rod 14.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A surgical instrument comprising:
   a first member extending along a longitudinal axis between a first end and a second end including a first jaw having a first inner surface;
   a second member comprising a second inner surface that defines a passageway having the first member disposed therein such that the first member is rotatable relative to the second member about the longitudinal axis, the second member extending between a first end and a second end including a second jaw having a third inner surface that faces the first inner surface and is spaced apart from the second inner surface; and a third member connected to the first end of the first member to relatively translate the second ends, the third member including a part and a locking element engageable with the part, wherein the part is disposable in a first locking orientation such that the first and third inner surfaces engage a spinal construct, a second locking orientation such that the part disengages the locking element and is biased relative to the third member and a non-locking orientation such that the part is moved relative to the third member and the second locking orientation such that the first and third inner surfaces disengage the spinal construct.

2. A surgical instrument as recited in claim 1, wherein the third member includes a handle body and the part includes a lever.

3. A surgical instrument as recited in claim 2, wherein the lever is rotatable relative to the handle body to the second locking orientation and the non-locking orientation.

4. A surgical instrument as recited in claim 2, wherein the lever is biased outwardly from the handle body to the second locking orientation.

5. A surgical instrument as recited in claim 1, wherein the part is manipulable from the second locking orientation to the non-locking orientation to translate the first member relative to the second member.

6. A surgical instrument as recited in claim 1, wherein the part includes a first lever biased outwardly to the second locking orientation and a second lever connected to the first lever, the second lever being manipulable from the second locking orientation to the non-locking orientation to translate the first member relative to the second member.

7. A surgical instrument as recited in claim 1, wherein the locking element is resiliently biased to the first locking orientation.

8. A surgical instrument as recited in claim 1, wherein the first member includes a first shaft and a second shaft engaged with the first shaft, the shafts being relatively movable to relatively translate the second ends for tensioning engagement with the spinal construct.

9. A surgical instrument as recited in claim 8, further comprising a detent lock engageable with the first shaft to selectively tension engagement with the spinal construct.

10. A surgical instrument as recited in claim 1, wherein the part includes a cam linkage engageable with the third member.

11. A surgical instrument as recited in claim 1, wherein the part includes a lever rotatable to an angle of substantially 30 degrees relative to a handle body of the third member.

12. A surgical instrument as recited in claim 1, wherein the first jaw has a maximum width that is greater than that of the passageway so as to prevent the first jaw from entering the passageway.

13. A surgical instrument as recited in claim 1, wherein:
the part comprises a first notch and the third member comprises a button that includes a second notch; and
the first notch engages the second notch when the part is in the first locking orientation and is spaced apart from the second notch when the part is in the second locking orientation and the non-locking orientation.

14. A surgical instrument comprising:
an inner shaft extending along a longitudinal axis between a first end and a second end having a first clamp, the first clamp including a first inner surface;

an outer sleeve comprising a second inner surface that defines a passageway having the inner shaft disposed therein such that the inner sleeve is rotatable relative to the outer sleeve about the longitudinal axis, the outer sleeve extending between a first end and a second end having a second clamp, the second clamp comprising a third inner surface that faces the first inner surface and is spaced apart from the second inner surface;

a handle body connected with the outer sleeve; and an actuator mounted with the handle body and including a first lever pivotally connected to a second lever that is connected to the first end of the inner shaft, the actuator further including a lock that is resiliently biased to engage the first lever, wherein the first lever is disposable in a first locking orientation such that the first and third inner surfaces engage a spinal construct, a second locking orientation such that the first lever disengages the lock and is biased to rotate relative to the handle body and a non-locking orientation such that the first lever is forcibly manipulated relative to the second locking orientation to rotate the second lever such that the clamps are disposed to disengage the spinal construct.

15. A surgical instrument as recited in claim 14, wherein the second lever includes a cam linkage engageable with the handle body.

16. A surgical instrument as recited in claim 14, wherein the inner shaft includes a first shaft and a second shaft engaged with the first shaft, the first and second shafts being relatively movable to relatively translate the first and second clamps for tensioning engagement with the spinal construct.

17. A surgical instrument as recited in claim 16, further comprising a detent lock engageable with the first shaft to selectively tension engagement with the spinal construct.

18. A surgical instrument as recited in claim 14, wherein the first lever rotates away from the handle body to the second locking orientation.

19. A surgical implant system comprising:
a surgical instrument comprising:
a first member extending along a longitudinal axis between a first end and a second end including a first jaw having a first inner surface,
a second member comprising a second inner surface that defines a passageway having the first member disposed therein such that the first member is rotatable relative to the second member about the longitudinal axis, the second member extending between a first end and a second end including a second jaw having a third inner surface that faces the first inner surface and is spaced apart from the second inner surface, and
a third member connected to the first end of the first member to relatively translate the second ends, the third member including a part and a locking element engageable with the part;
a spinal rod,
wherein the part is disposable in a first locking orientation such that the first and third inner surfaces engage the spinal rod, a second locking orientation such that the part disengages the locking element and is biased relative to the third member and a non-locking orientation such that the part is moved relative to the third member and the second locking orientation such that the first and third inner surfaces disengage the spinal rod; and
an extender including a first wall and a second wall, the walls defining an implant cavity therebetween, the implant cavity defining a first width dimension between the walls.

20. A surgical implant system as recited in claim 19, wherein the second end of the second member includes a second width dimension greater than the first width dimension to prevent disposal of the second end of the second member within the implant cavity.

\* \* \* \* \*